United States Patent
Muenk et al.

(10) Patent No.: US 7,312,031 B1
(45) Date of Patent: Dec. 25, 2007

(54) ALPHA-COMPLEMENTATION VIRAL FUSION ASSAY

(75) Inventors: Carsten Muenk, Frankfurt (DE); Anne Holland, San Diego, CA (US); Nathaniel Landau, San Diego, CA (US)

(73) Assignee: The Salk Institute for Biological Studies, San Diego, CA (US)

( * ) Notice: Subject to any disclaimer, the term of this patent is extended or adjusted under 35 U.S.C. 154(b) by 112 days.

(21) Appl. No.: 10/729,069

(22) Filed: Dec. 4, 2003

Related U.S. Application Data

(60) Provisional application No. 60/431,298, filed on Dec. 6, 2002.

(51) Int. Cl.
*C12Q 1/70* (2006.01)
*G01N 33/567* (2006.01)

(52) U.S. Cl. .......................... 435/5; 435/7.21
(58) Field of Classification Search ................ 435/7.1, 435/7.2, 7.23
See application file for complete search history.

(56) References Cited

U.S. PATENT DOCUMENTS

| | | | |
|---|---|---|---|
| 5,444,161 A | 8/1995 | Manning et al. | 536/4.1 |
| 6,096,917 A | 8/2000 | Hornback et al. | 560/43 |
| 6,100,426 A | 8/2000 | Mauldin et al. | 562/440 |
| 6,103,922 A | 8/2000 | Hornback et al. | 560/43 |
| 6,103,923 A | 8/2000 | Mauldin et al. | 560/43 |
| 6,124,494 A | 9/2000 | Mauldin et al. | 560/43 |
| 6,127,422 A | 10/2000 | Colacino et al. | 514/569 |
| 6,156,924 A | 12/2000 | Hornback et al. | 560/43 |
| 6,175,034 B1 | 1/2001 | Mauldin et al. | 560/5 |
| 6,180,815 B1 | 1/2001 | Mauldin et al. | 560/5 |
| 6,180,816 B1 | 1/2001 | Mauldin et al. | 560/5 |

OTHER PUBLICATIONS

Bieniasz et al. HIV-1 induced cell fusion is mediated by multiple regions within both the viral envelope and the CCR-5 co-receptor 1997. Th EMBO Journal vol. 16, No. 10, pp. 2599-2609.*
Wigley et al. Protein solubility and folding monitored in vivo by structural complementation of a genetic marker protein 2001. Nature Biotechnology vol. 19, pp. 131-136.*
Isaacs et al. A macrophage fusion assay for rapid screening of cloned HIV-1 Env using dual recombinant vaccinia viruses expressing distinct RNA polymerases 1999. Journal of Virological Methods vol. 81, pp. 55-61.*
Mohler W. Gene expression and cell fusion analyzed by lacZ complementation in mammalian cells. Proceedings from National Academy of Science USA. Oct. 1996, vol. 93, pp. 12423-12427.*
Moir S. Expression of HIV env gene in a human T cell line for a rapid and quantifiable cell fusion assay. AIDS Research and Human Retroviruses. 1996, vol. 12, No. 9, pp. 811-820.*
Doranz et al. A Small-molecule Inhibitor Directed against the Chemokine Receptor CXCR4 Prevents its Use as an HIV-1 Coreceptor. J. Exp. Med. Oct. 20, 1997, vol. 186, No. 8, p. 1395-1400.*
Allaway et al., *AIDS Res. Hum. Retrovir.* 11:533-539 (1995).
Baba et al., *Proc. Nat'l. Acad. Sci. U.S.A.* 96(10):5698-5703 (1999).
Chan et al., *Cell* 89:263-273 (1987).
Dalgleish et al., *Nature* 312:763-767 (1984).
Deng et al., *Nature* 381:661-666 (1996).
Donzella et al., *Nat. Med.* 4:72-77 (1998).
Dutch et al., *Biosci. Rep.* 20(6):597-612 (2000).
Graham et al., *Virol.* 52:456-67 (1973).
Hammarskjold et al., *Biochem. Biophys. Acta.* 989:269-280 (1989).
Hope et al., *Proc. Nat'l. Acad. Sci. U.S.A.* 87:7787-91 (1990).
Klatzmann et al., *Nature* 312:767-768 (1984).
Langley and Zabin, *Biochemistry* 15:4866 (1976).
Lenburg and Landau, *J. Virol.* 67:7238-45 (1993).
Light et al., *J. Biol. Chem.* 249:2285 (1974).
Maddon et al., *Cell* 42:93-104 (1985).
Maddon et al., *Cell* 47:333-348 (1986).
McDougal et al., *Science* 231:382-385 (1986).
Moosmann and Rusconi, *Nucleic Acids Res.* 24(6):1171-1172 (1996).
Morgenstern and Land, *Nucleic Acids Res.* 18(12):3587-96 (1990).
Onishi et al., *Exp. Hematol.* 24:324-329 (1996).
Overbaugh et al., *Microbiol. & Mol. Biol. Rev.* 65:371-389 (2001).
Raviv et al., *Virology* 293:243-51. (2002).
Richards and Vithayathil, *J. Biol. Chem.* 234:1459-1465 (1959).
Söllner et al., *Nature* 362:318-24 (1993).
Strizki et al., *Proc. Nat'l. Acad. Sci. U.S.A.* 98(22):12718-12723 (2001).
Sutton et al., *Nature* 395:347-53 (1998).
Vodicka et al., *Virology* 233:193-98 (1997).
Wild et al., *Proc. Nat'l. Acad. Sci. U.S.A.* 91(21):9770-9774 (1994).
York-Higgins et al., *J. Virol.* 64:4016-4020 (1990).
Moosmann and Rusconi, *Nucleic Acids Research*, 24(6):1171-1172 (1996).
Richard Horuk, et al., "The CC Chemokine I-309 Inhibits CCR8-dependent Infection by Diverse HIV-1 Strains", The Journal of Biological Chemistry, Jan. 2, 1998, 273(1), pp. 386-391.

* cited by examiner

*Primary Examiner*—Jeffrey S. Parkin
*Assistant Examiner*—Louise Humphrey
(74) *Attorney, Agent, or Firm*—Grant Anderson LLP; Bruce D. Grant

(57) ABSTRACT

The present invention relates to the use of an alpha complementation assay as a quick, effective, and safe method for the detection of cell fusion mediated by viral proteins. Additionally, the method disclosed herein permits the identification of inhibitors of cell fusion using an alpha complementation assay.

19 Claims, 13 Drawing Sheets

ALPHA-COMPLEMENTATION VIRAL FUSION ASSAY

CROSS-REFERENCE TO RELATED APPLICATIONS

This application claims benefit of U.S. provisional Application No. 60/431,298, filed Dec. 6, 2002. The content of that application is incorporated herein by reference in its entirety.

STATEMENT OF GOVERNMENT INTEREST

This invention was supported in part by NIH Grant Nos. R01 AI43252 and 7 R01 AI42397. The United States government has certain rights in this invention.

FIELD OF THE INVENTION

The invention relates to methods of detecting cell fusion and inhibitors thereof.

BACKGROUND

The entry of an enveloped virus into a target cell is initiated by the envelope protein of the virus binding to a receptor on the target cell membrane. The interaction of the receptor and the viral envelope protein triggers fusion between the envelope protein and the cell membrane, permitting the entry of the viral genome into the cytoplasm of the cell. The fusion mediated by the viral envelope protein also permits cell-to-cell transmission of enveloped viruses. The expression of the viral envelope protein on the membrane of an infected cell can trigger fusion with an uninfected cell bearing the appropriate viral envelope protein receptor, further increasing the virulence of the virus within the host. Perhaps the most well-known example of the contribution of viral-mediated cell fusion to a disease state is the viral-induced fusion that results in the formation of multinucleated giant cells (synctia) after human immunodeficiency virus (HIV) infection, which eventually leads to death of the fused cells. Thus, the receptor-viral envelope protein determines the tropism, virulence, and ultimately the pathogenicity of the virus in a particular host.

Structural, biochemical, and functional studies have revealed a number of common features for viral membrane fusion proteins. At least two groups of fusion proteins have been identified to date. Dutch, R. E., et al., *Biosci. Rep.* 20: 597-612 (2000). In one group, the fusion proteins that include the paramyxovirus F protein, the HIV gp 160 protein, the HTLV SU protein, the Ebola GP protein, and the influenza hemagglutin (HA) protein. These viral envelope proteins share common features that include multiple glycosylation sites, a trimeric structure, and proteolytic cleavage for fusogenic activation. For each of the fusion proteins, the proteolytic cleavage resulted in an extremely hydrophobic subunit near the new N-terminus identified as the fusion peptide. Three heptad repeats were identified near the fusion peptide and the transmembrane domain that formed a trimeric coiled coil. Therefore, within widely disparate groups of enveloped viruses, a common mechanism of viral membrane fusion appears to function using the trimeric coiled coil motif. In a second group that includes togavirus, rhabodovirus, and flavivirus, fusion appears to occur by another molecular mechanism.

Membrane fusion events may be mediated by interaction of the viral envelope protein with one or more receptors on a target cell. For example, a single protein serves both as the viral cell recognition and fusion proteins (e.g., influenza) whereas in other viruses, these activities are separated (e.g., HIV). Alternately stated, the viral envelope protein can sometimes require both a receptor and a co-receptor for the initiation of fusion events. See, e.g., Overbaugh, et al., *Microbiol. & Mol. Biol. Rev.* 65:371-389 (2001). To date, only HIV has been shown to use co-receptors to mediate the fusogenic event. Additionally, membrane fusion may occur under pH-independent or pH-dependent conditions.

In one example of viral fusion, the entry of HIV into target cells is mediated by a fusion reaction in which the gp120/gp41 glycoprotein of the virus binds to CD4 and a CC chemokine receptor, CCR5 or CXCR4, on the target cell membrane. The HIV enveloped surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains non-covalently associated with gp41, possibly in a trimeric or multimneic form. Hammarskjold, M. et al., *Biochem. Biophys. Acta* 989:269-280 (1989). HIV is targeted to CD4+ cells because the CD4 cell surface protein acts as the cellular receptor for the HIV-I virus. See, e.g., Dalgleish, A. et at, *Nature* 312:763-767 (1984); Klatzmann et al., *Nature* 312: 767-768 (1984). Viral entry into cells is dependent upon gp120 binding the cellular CD4+ receptor molecules. See (McDougal, J. S. et al., *Science* 231:382-385 (1986); Maddon, P. J. et al., *Cell* 47:333-348 (1986).

The tropism and virulence of HIV appears to be determined by the co-receptor used to bind the viral envelope protein. HIV strains using the CCR5 as a co-receptor mediate transmission and predominate early in the course of disease, while those using CXCR4 are mainly associated with the symptomatic phase. HIV pathogenesis is very sensitive to cell surface CCR5 levels. Individuals who are homozygous for the CCR5 null allele D32 are resistant to infection. Heterozygotes for this allele, although not protected from infection, experience a delay of about two years in the onset of disease symptoms. This is apparently a result of the rather modest 50% reduction in cell surface CCR5 compared to wild-type CCR5 cells.

Membrane fusion also occurs as part of the intracellular vesical machinery. These membrane processes permit the transport of material between cellular compartments and out of the cell. This fusion process is mediated by a set of conserved proteins collectively termed SNARES. Solinar et al., *Nature* 362: 318-24 (1993). The proteins mediating the fusogenic activity also have a coiled coil motif similar to that of viral envelope proteins. Sutton, et al., *Nature* 395: 347-53.

BRIEF SUMMARY

Provided herein are compositions and methods useful for detection of the presence or absence of cell fusion as well as methods for identifying cell fusion inhibitors. These methods provide a means to directly detect envelope glycoprotein-mediated fusion. Moreover, the methods for rapid and simple testing provided herein do not require live virus and thus can be performed without biohazard containment.

Also, provided herein is a method for detecting the presence or absence of cell fusion, which comprises contacting a first cell with a second cell. The first cell comprises a first reporter molecule fragment and a viral envelope protein while the second cell comprises a second reporter molecule fragment and a viral envelope protein receptor capable of binding to the viral envelope protein of the first cell. The first reporter molecule fragment and the second reporter molecule fragment of the first and second cells, respectively, combine to form a functional reporter molecule upon fusion of the first cell with the second cell. The presence or absence of the functional reporter molecule is detected using a signal generated by the reporter molecule, whereby the presence of a signal indicates the presence of cell fusion and, conversely, the absence of a signal indicates the absence of cell fusion.

Also, provided herein is a method for identifying a cell fusion inhibitor molecule, which comprises contacting a system comprising a first cell and a second cell with a test molecule. The first cell comprises a first reporter molecule fragment and a viral envelope protein while the second cell comprises a second reporter molecule fragment and a viral envelope protein receptor capable of binding to the viral envelope protein of the first cell. The first reporter molecule fragment and the second reporter molecule fragment of the first and second cells, respectively, combine to form a functional reporter molecule upon fusion of the first cell with the second cell. The presence or absence of a functional reporter molecule is detected by the presence or absence of a signal generated by the functional reporter molecule. The test molecule is identified as a cell fusion inhibitor molecule when the signal produced by the functional reporter molecule in the system contacted with the test molecule is different than the signal produced in a system not contacted by the test molecule.

Further, provided herein is a cell fusion inhibitor molecule identified by the above method.

Provided herein is a cell which comprises a first reporter molecule fragment and a viral envelope protein, where the cell is capable of fusing with a second cell which comprises a second reporter molecule fragment and a viral envelope protein receptor capable of binding to the viral envelope protein of the cell; and the first reporter molecule fragment and the second reporter molecule fragment combine to form a functional reporter molecule upon fusion of the cell with the second cell.

Also, provided herein is a cell which comprises a first reporter molecule fragment and a viral envelope protein receptor, where the cell is capable of fusing with a second cell which comprises a second reporter molecule fragment and a viral envelope protein capable of binding to the viral envelope protein receptor of the cell; and the first reporter molecule fragment and the second reporter molecule fragment combine to form a functional reporter molecule upon fusion of the cell with the second cell.

Further, provided herein is a composition comprising a) a first cell which comprises a first reporter molecule fragment and a viral envelope protein, where the cell is capable of fusing with a second cell which comprises a second reporter molecule fragment and a viral envelope protein receptor capable of binding to the viral envelope protein of the cell; and b) the second cell which comprises the second reporter molecule fragment and the viral envelope protein receptor capable of binding to the viral envelope protein of the cell; and the first reporter molecule fragment and the second reporter molecule fragment combine to form a functional reporter molecule upon fusion of the cell with the second cell.

Provided herein is a cell hybrid that is a fusion product of a first cell and second cell, which comprises a functional reporter molecule formed from the combination of a first reporter molecule fragment and a second reporter molecule fragment; a viral envelope protein; and a viral envelope protein receptor capable of binding to the viral envelope protein.

Also provided herein is a method of making a first cell, which comprises contacting a cell with a first expression construct containing a suitable promoter operably linked to a viral envelope protein coding sequence, whereby the viral envelope protein is expressed in a functional form on a cell surface; and contacting a cell with a second expression construct containing a suitable promoter operably linked to a first reporter molecule fragment coding sequence, whereby the reporter molecule fragment is expressed. Also provided herein is a method of making a second cell, which comprises contacting a cell with a first expression construct containing a suitable promoter operably linked to a viral envelope protein receptor coding sequence, whereby the viral envelope protein is expressed in a functional form on a cell surface; and contacting a cell with a second expression construct containing a suitable promoter operably linked to a second reporter molecule fragment coding sequence, whereby the reporter molecule fragment is expressed.

DETAILED DESCRIPTION

The alpha complementation assay provided herein is a quick, effective, and safe method for the detection of cell fusion and can be used to identify inhibitors of cell fusion. The alpha complementation assay is based on an enzyme whose functional activity comprises two or more separable portions or subunits. Expression of each portion alone will not result in enzymatic activity. However, co-expression of the separate portions restores the functional activity of the enzyme. Therefore, if two cells each separately express one portion of such an enzyme, detectable enzymatic activity will be observed only in the presence of cell fusion because cell fusion will permit the portions to be co-expressed.

Figure 1:
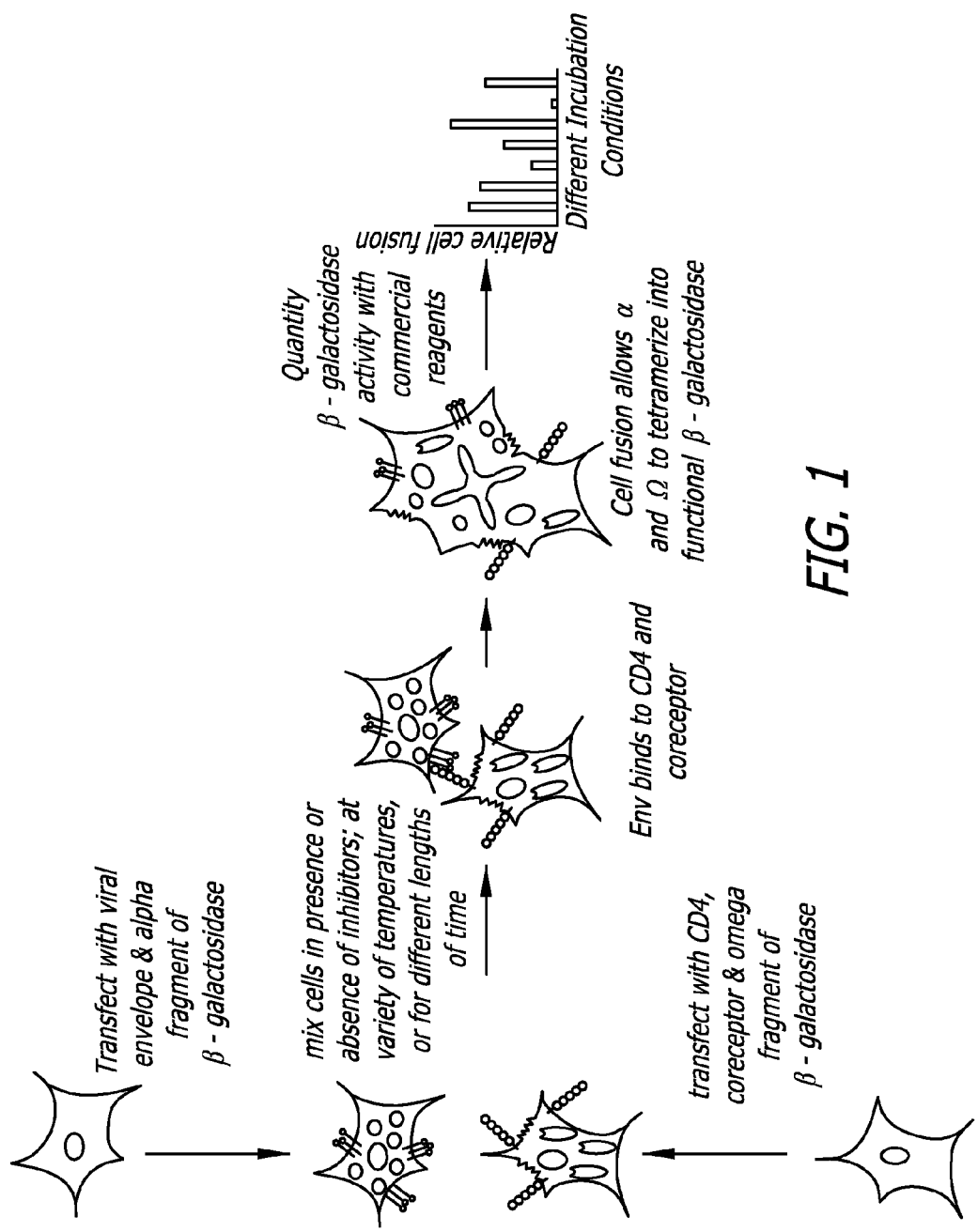
FIG. 1 is a schematic of a fusion assay.
Figure 2:
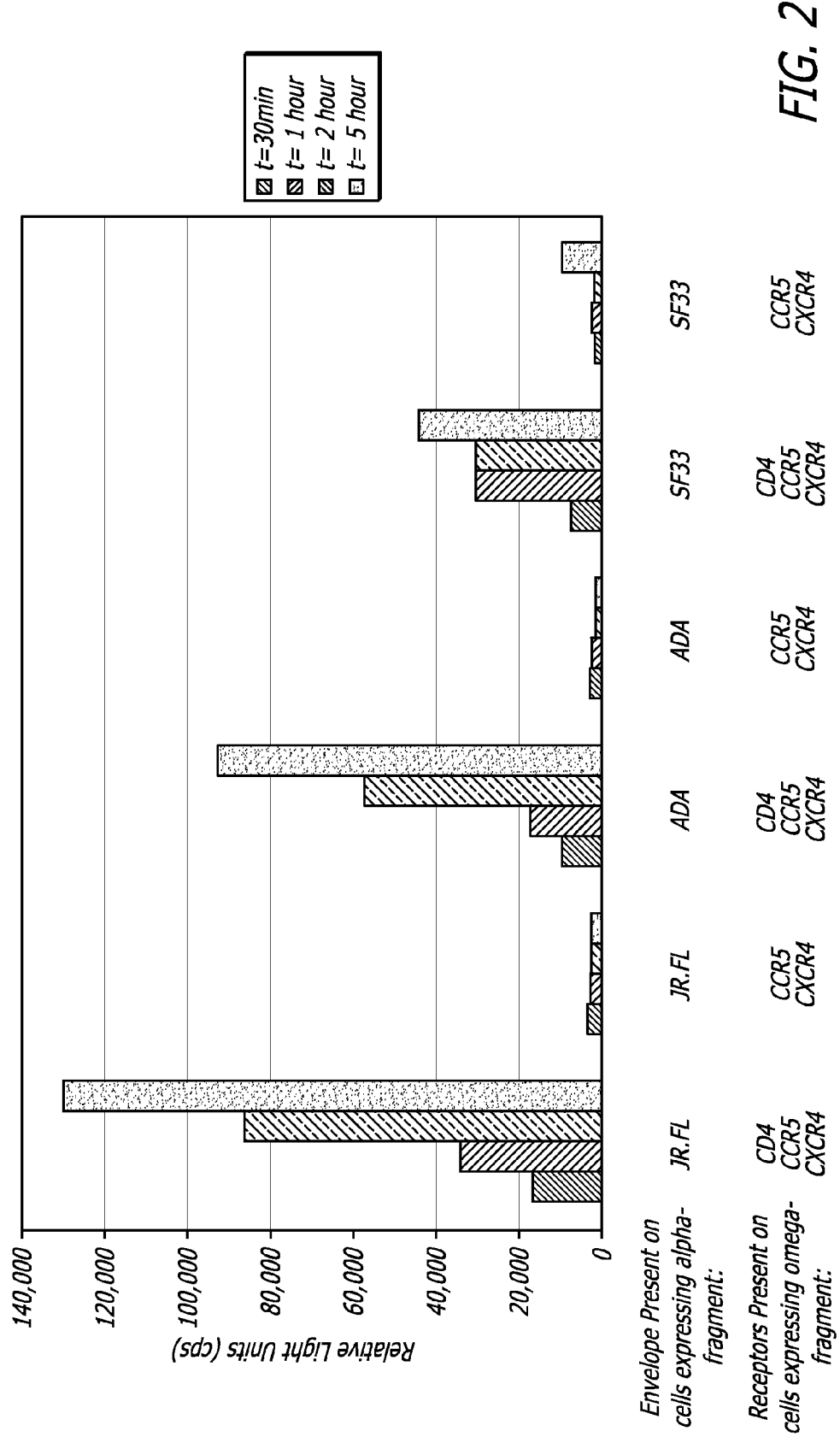
FIG. 2 depicts CD4-dependent HIV envelope-mediated cell fusion.
Figure 3:
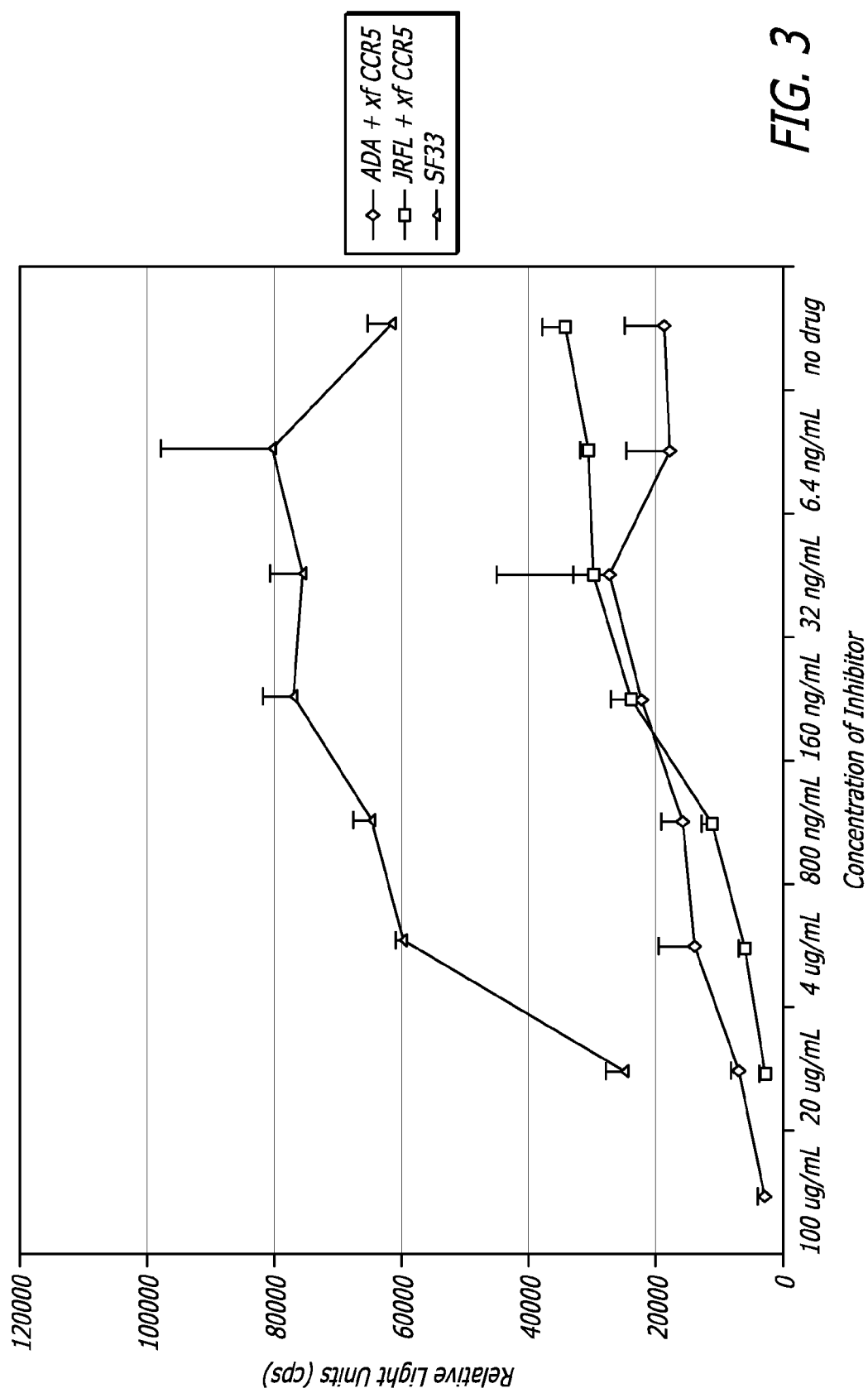
FIG. 3 depicts CD4-Ig inhibition of fusion reaction between 293T/alpha/Env Cells and 293T.Ω.CD4.3 cells. A soluble form of CD4 inhibits the fusion reaction in a concentration-dependent manner. Both CCR5- and CXCR4-tropic envelopes are affected.
Figure 4:
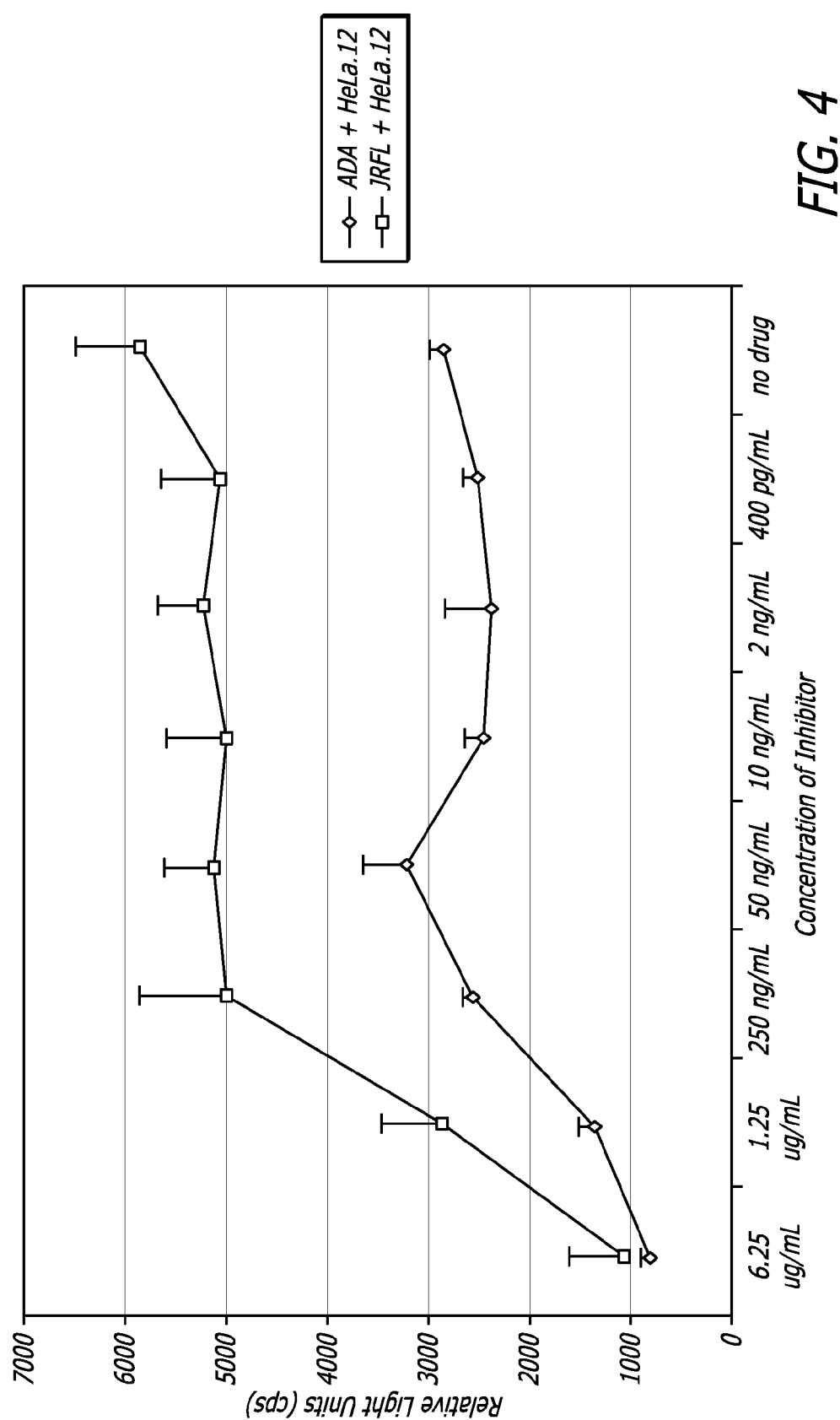
FIG. 4 depicts T-20 Peptide inhibition of fusion reaction between 293T/alpha/Env Cells and HeLa.Ω.CD4.CCR5 clone 12 cells. T-20 peptide, a peptide binding the gp41 subunit of the HIV envelope protein, inhibits the fusion reaction in a concentration-dependent manner. Both CCR5- and CXCR4-tropic envelopes are affected.
Figure 5:
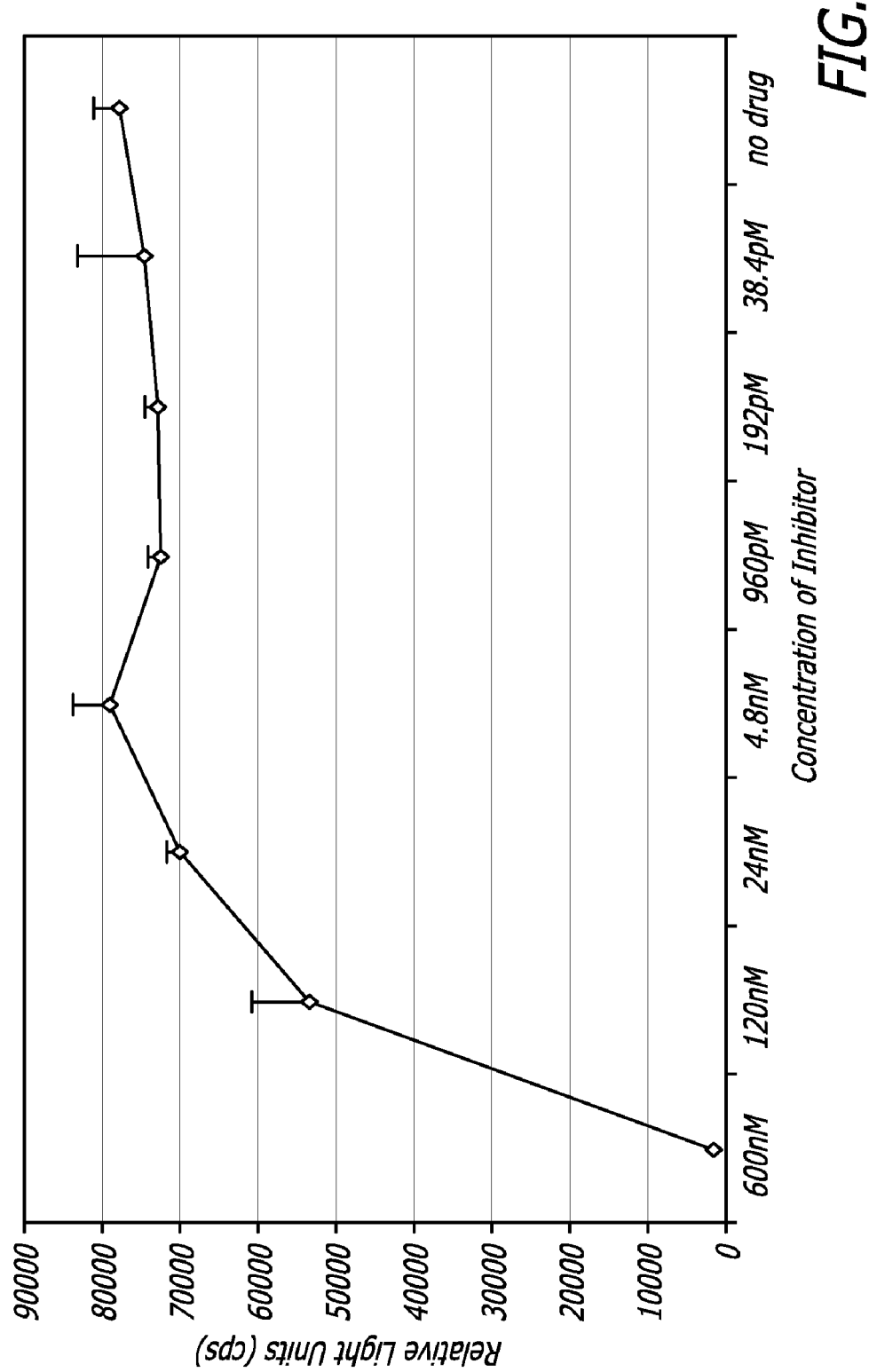
FIG. 5 depicts fusion of 293T.CD4.Ω with 293T/SF33 in the presence of C34 peptide. CD34 peptide, a peptide binding the gp41 subunit of HIV envelope, inhibits the fusion reaction in a concentration-dependent manner.
Figure 6:
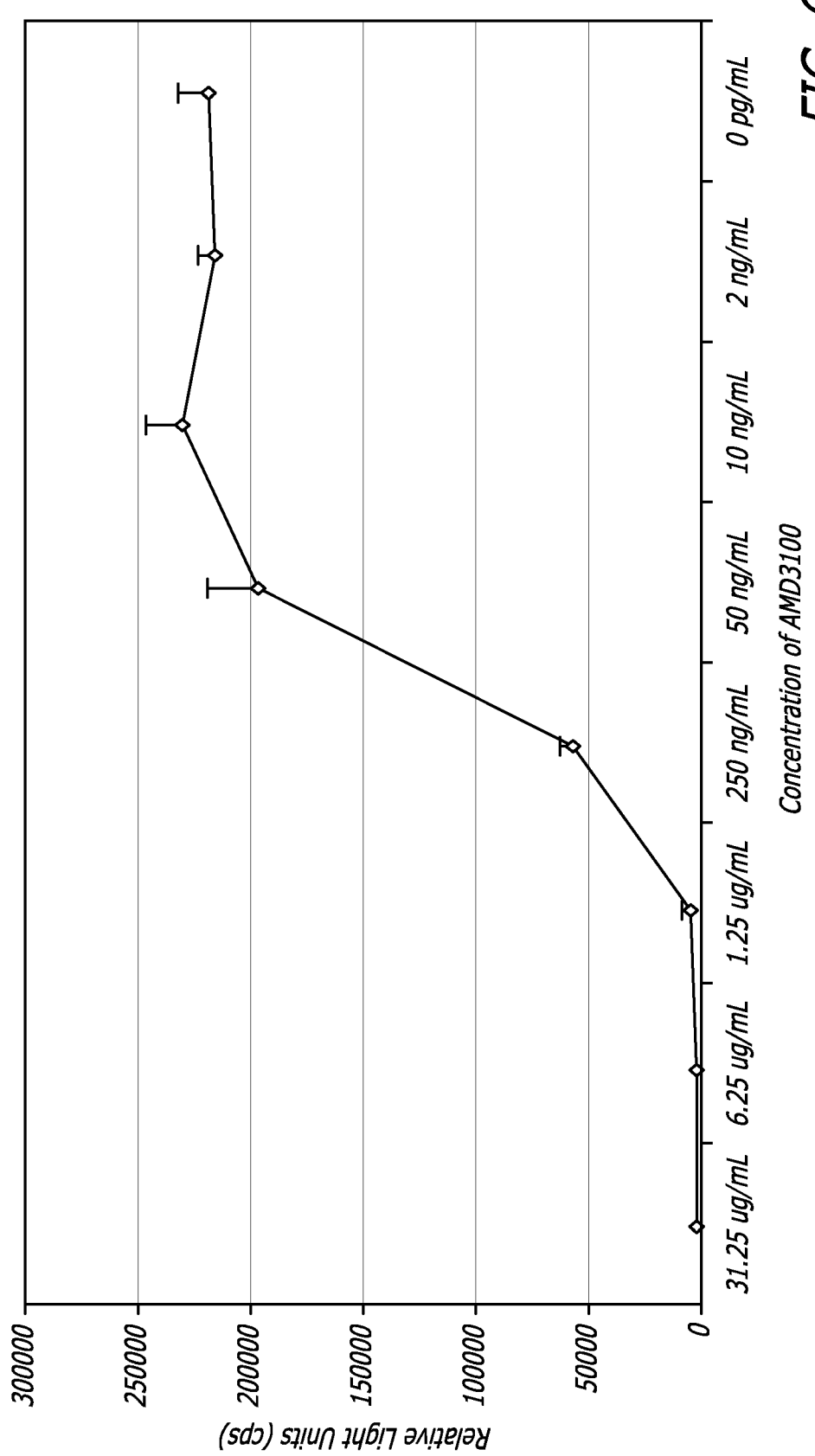
FIG. 6 depicts titration of AMD3100 in transfected SF33 Env and stable 293T.Ωcell line. AMD3100, a small molecule binding the second extracellular loop of CXCR4, inhibits the fusion reaction in a concentration-dependent manner.
Figure 7:
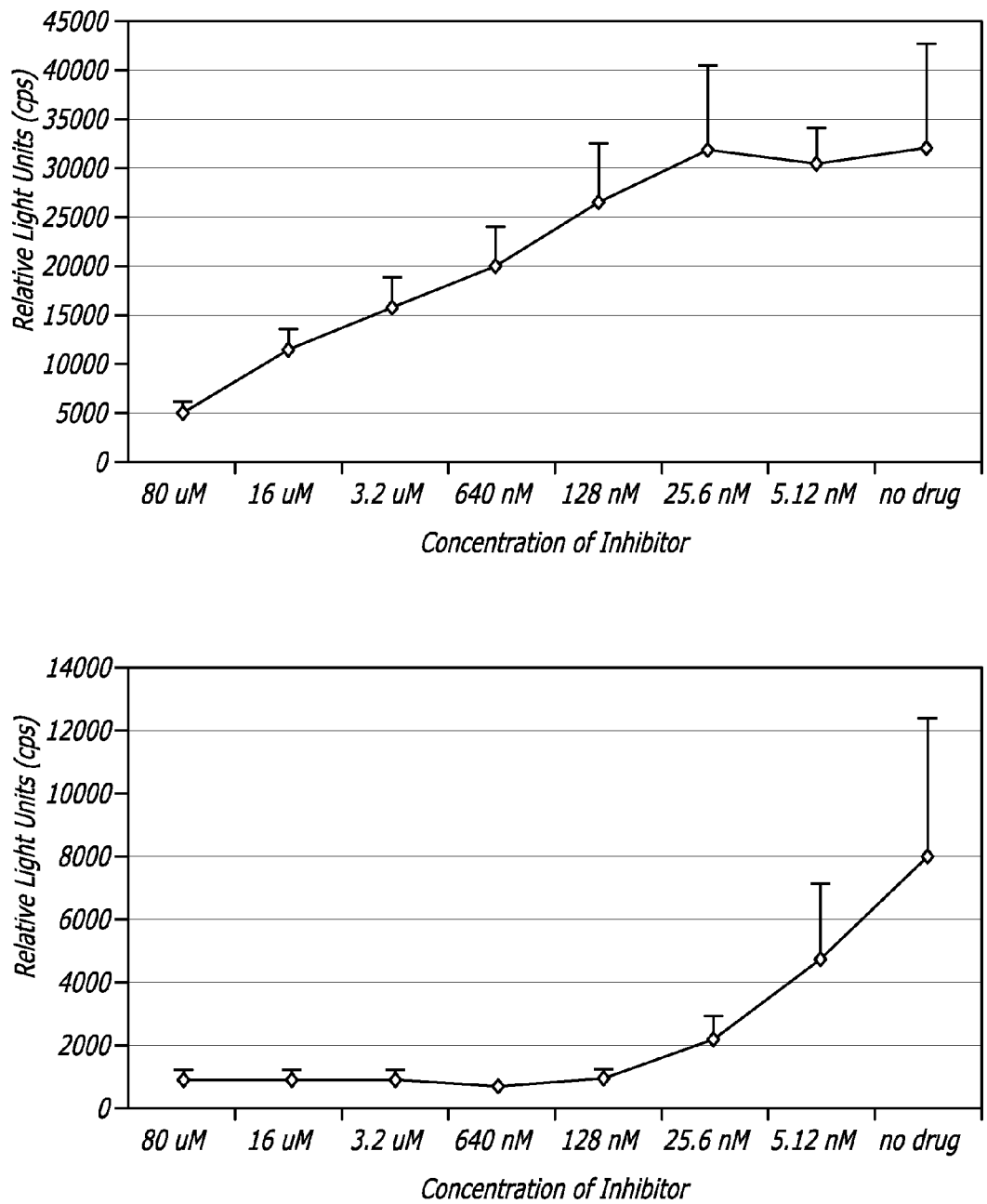
FIG. 7 depicts the fusion of 293T.CD4.Ω/CCR5 with 293T/ADA in the presence of TAK-779. TAK-779, a small molecule binding CCR5, inhibits the fusion reaction in a concentration-dependent manner.
Figure 8:
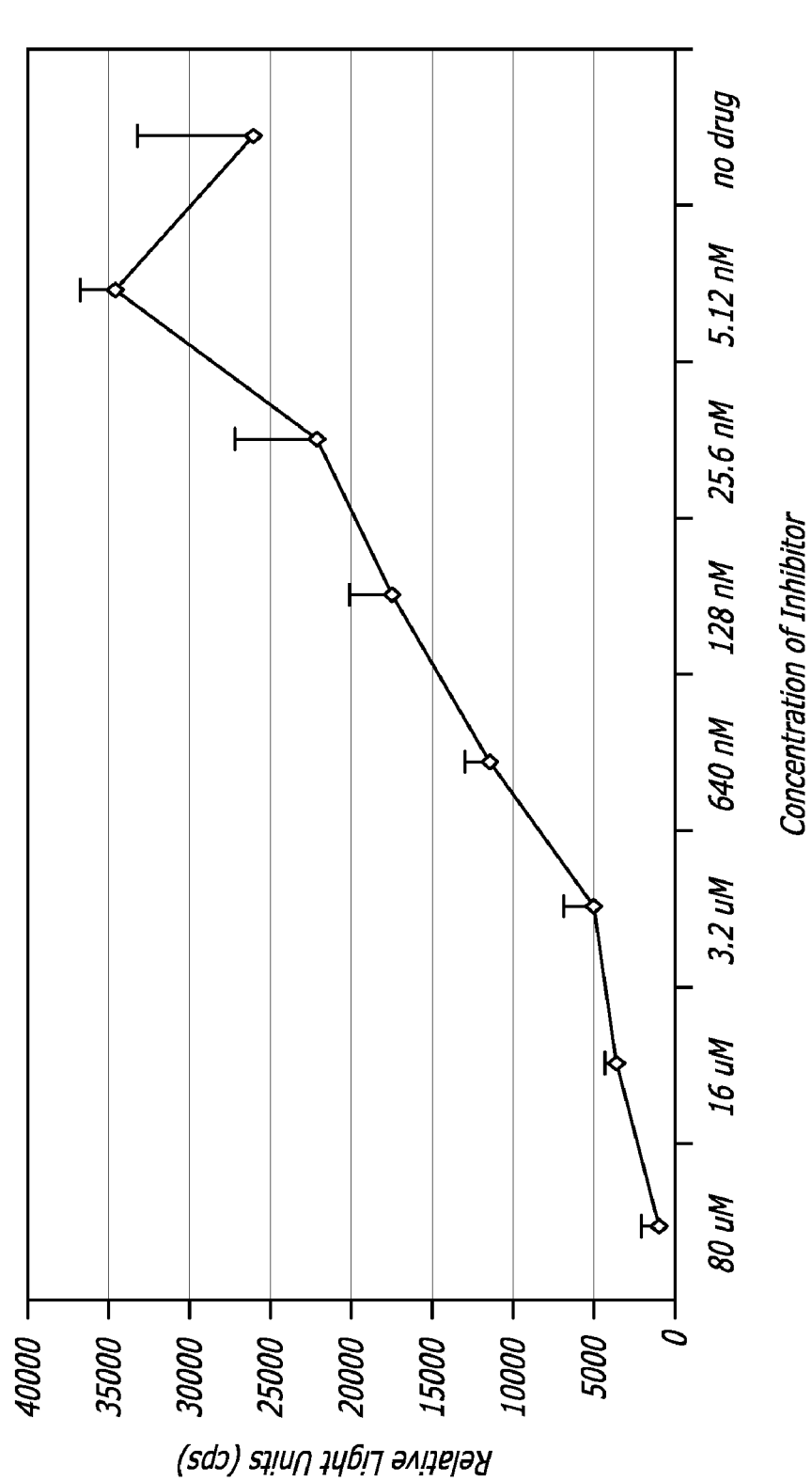
FIG. 8 depicts the fusion of 293T.CD4.Ω/CCR5 with 293T/ADA in the presence of GSK compound A. A small molecule binding CCR5 inhibits the fusion reaction in a concentration-dependent manner.
Figure 9:
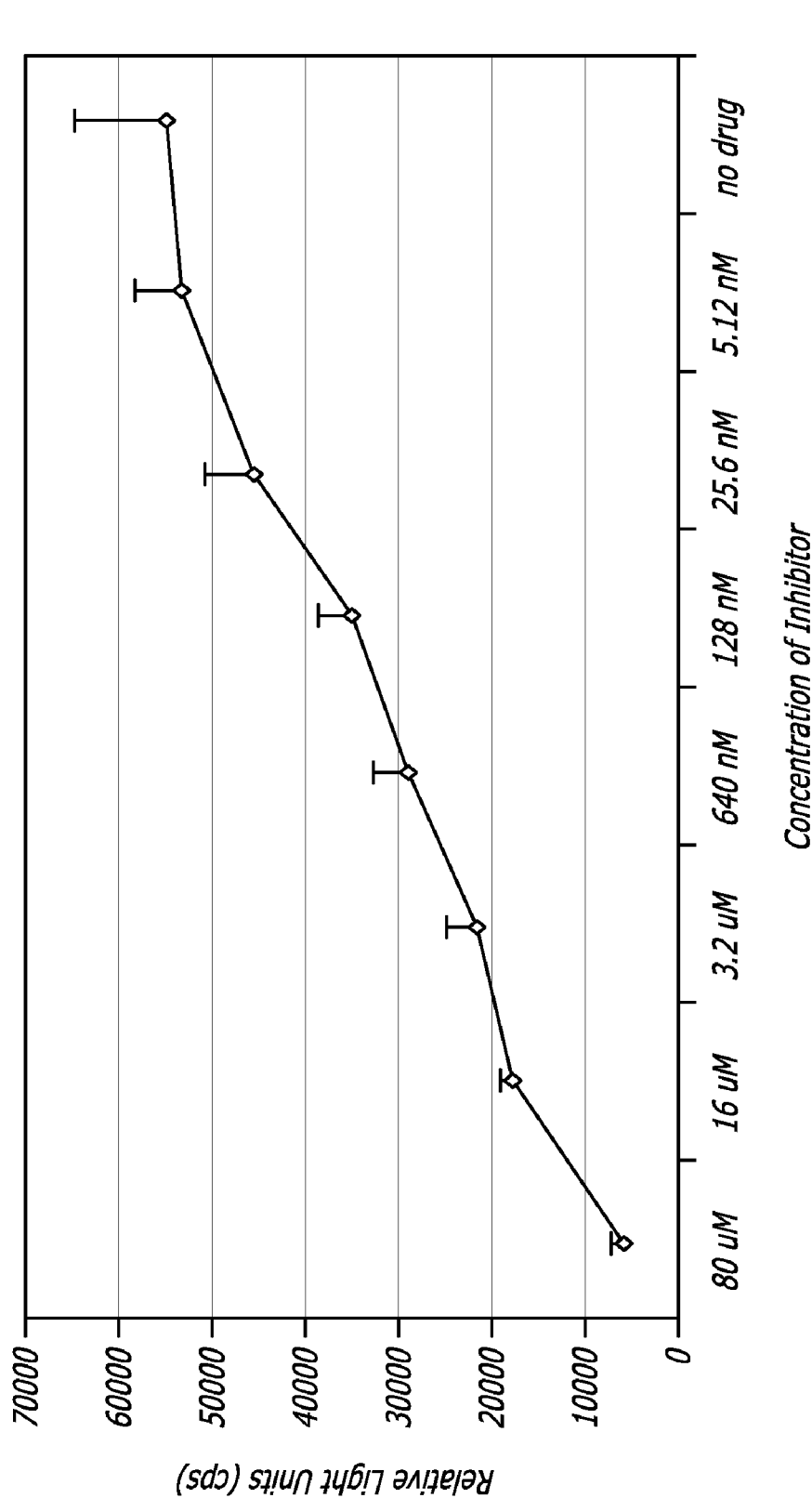
FIG. 9 depicts the fusion of 293T.CD4.Ω/CCR5 with 293T/ADA in the presence of GSK compound B. A small molecule binding CCR5 inhibits the fusion reaction in a concentration-dependent manner.
Figure 10:
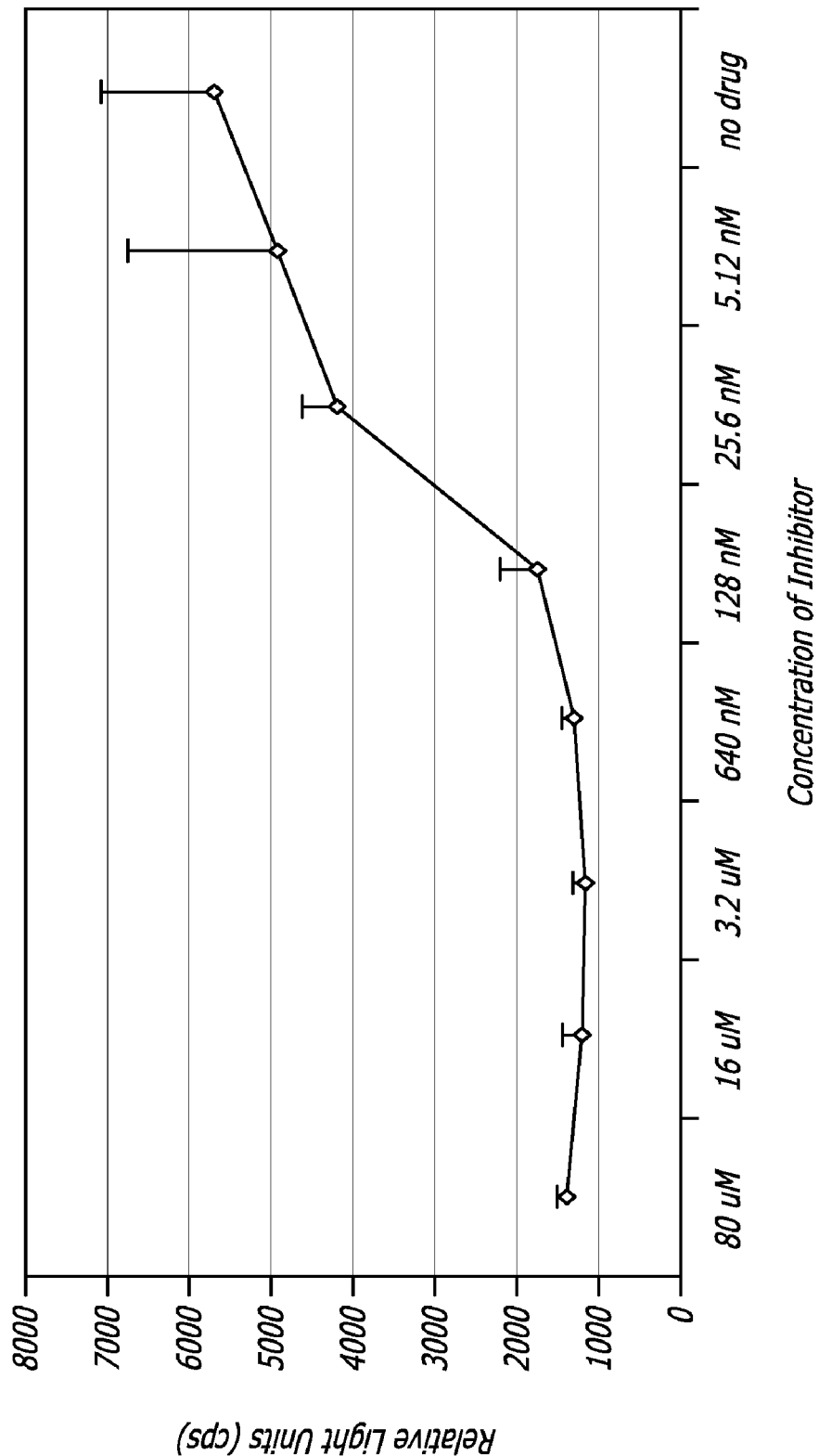
FIG. 10 depicts the fusion of HeLa.CD4.Ω.CCR5 clone 12 with 293T/ADA in the presence of GSK compound D. A small molecule binding CCR5 inhibits the fusion reaction in a concentration-dependent manner.
Figure 11:
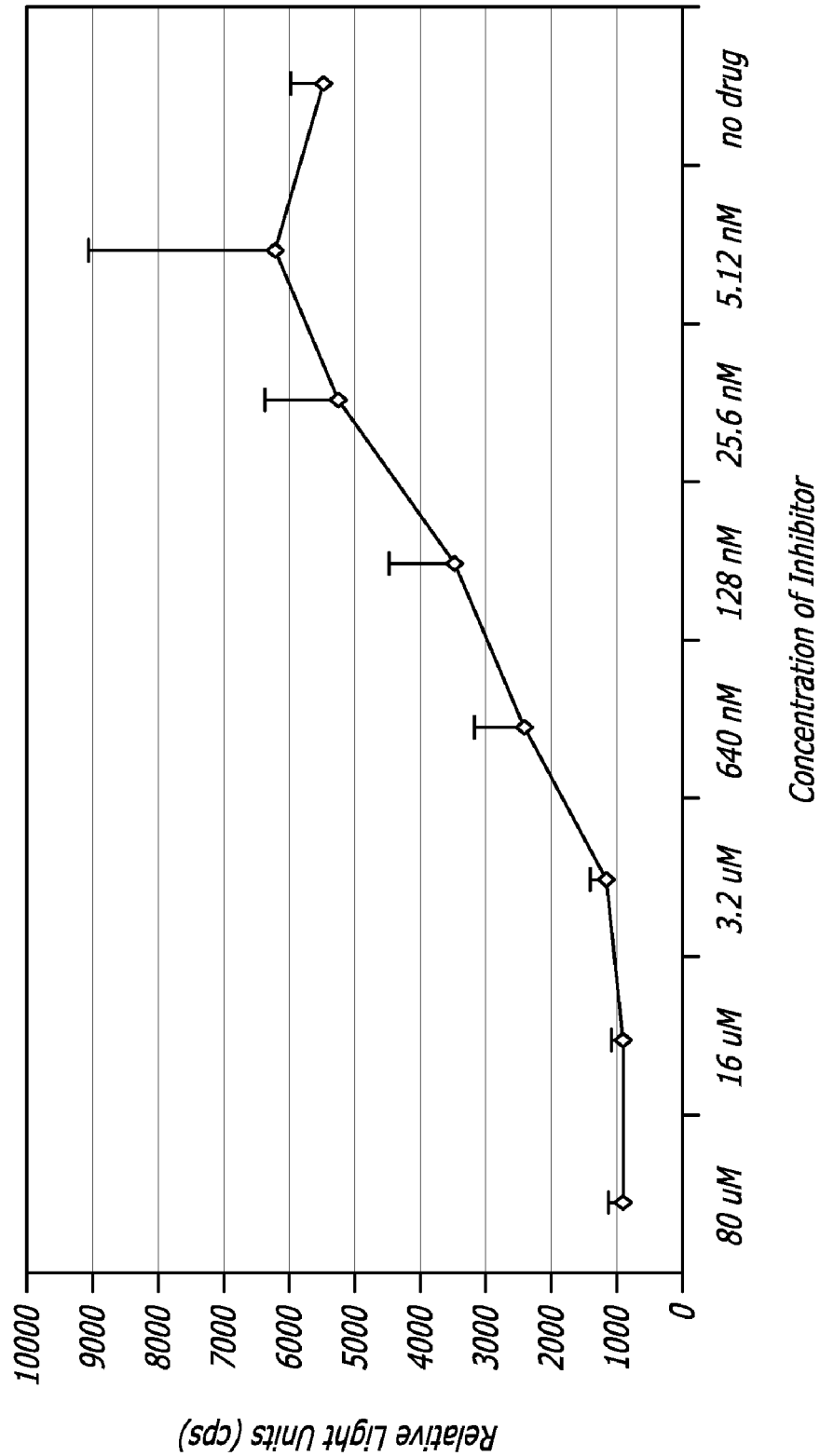
FIG. 11 depicts the fusion of HeLa.CD4.Ω.CCR5 clone 12 with 293T/ADA in the presence of GSK compound C. A small molecule binding CCR5 inhibits the fusion reaction in a concentration-dependent manner.
Figure 12:
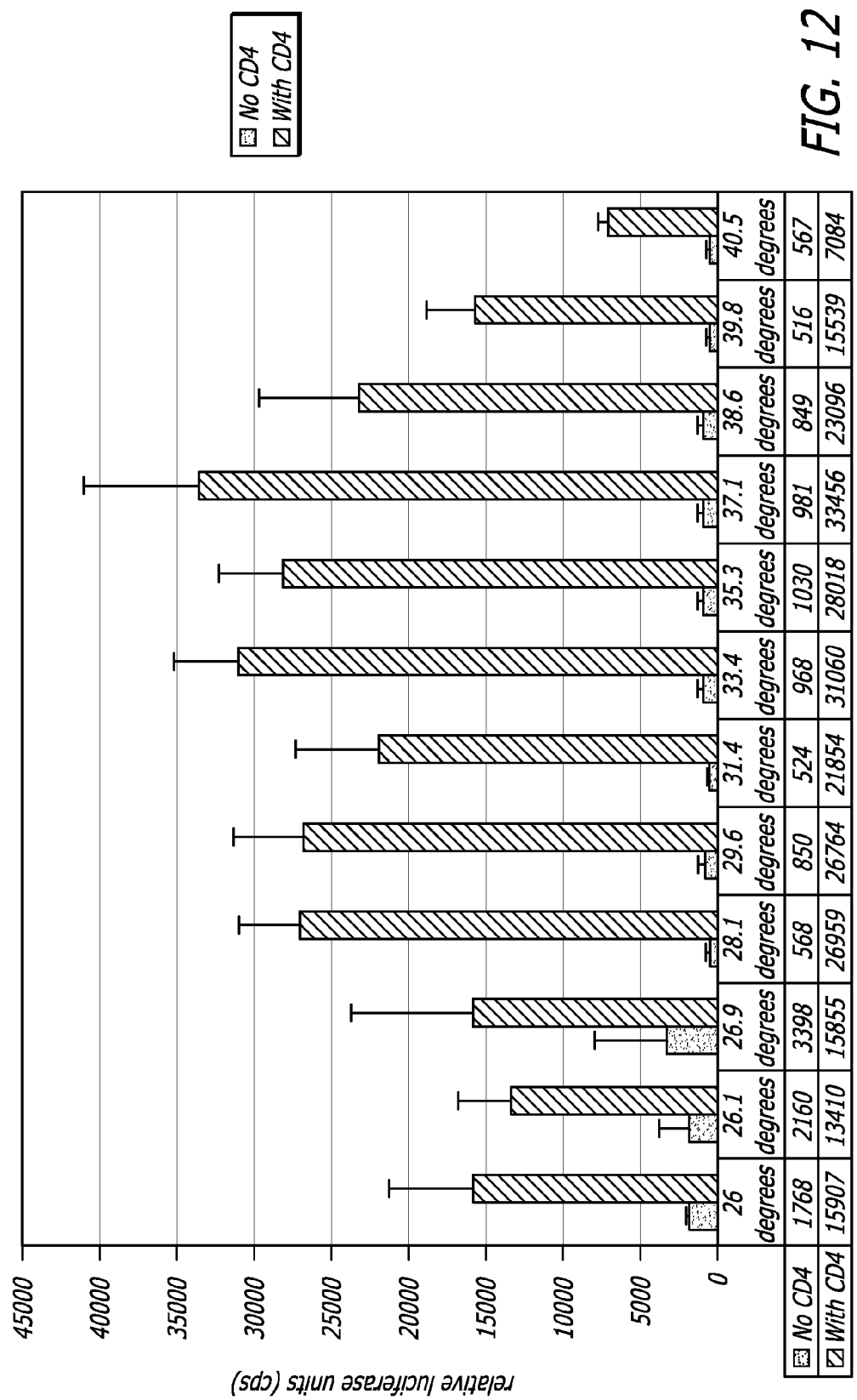
FIG. 12 depicts the fusion of 293T/Q Cells with 293T/alpha/SF33 at a range of temperatures for 4 hours.
Figure 13:
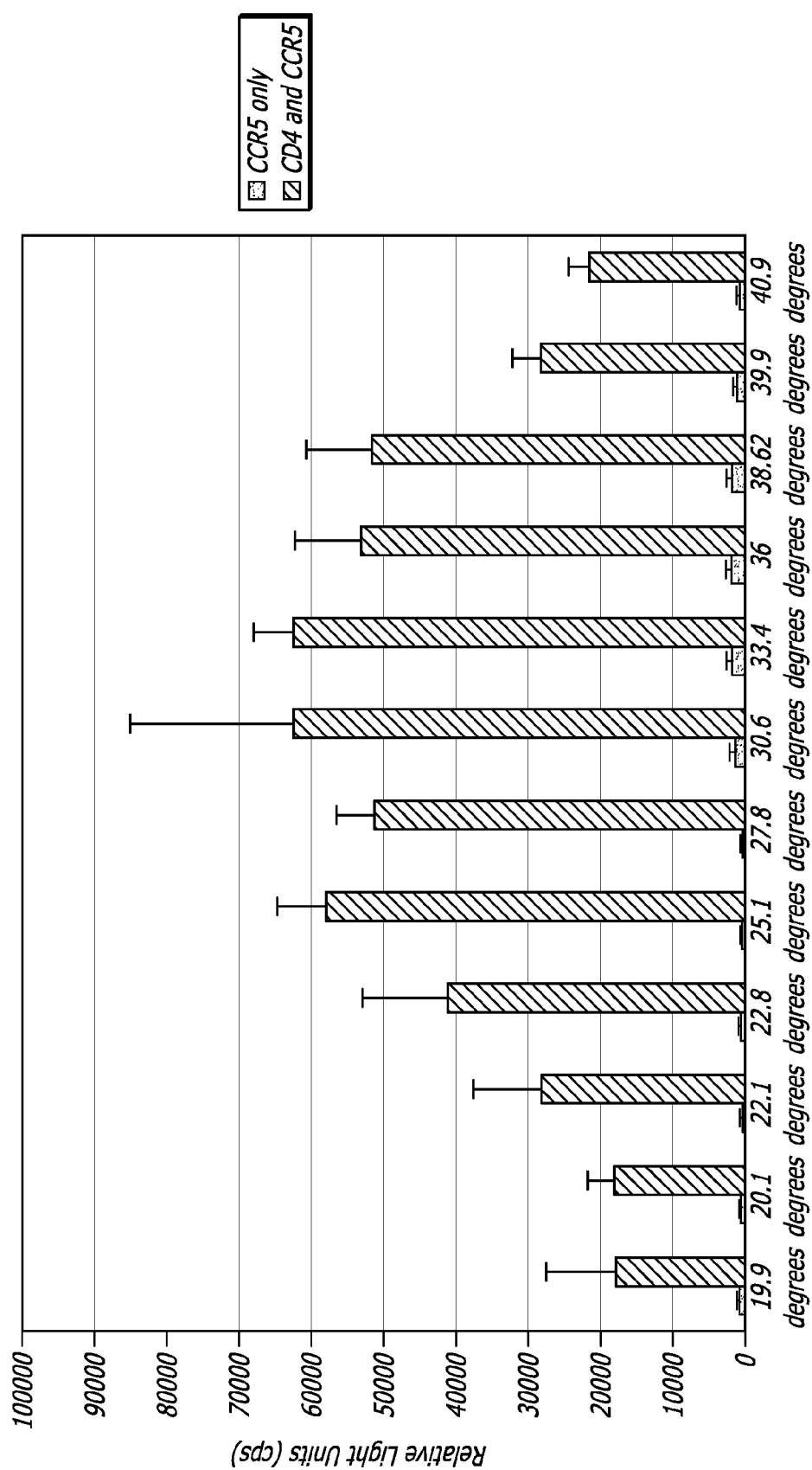
FIG. 13 depicts CCR5-tropic envelope fusion over a range of temperature.

One embodiment of the alpha complementation assay is shown in FIG. 1. A first cell is transfected with one or more constructs encoding a viral envelope (i.e., gp160) and the α-fragment of β-galactosidase. A second cell is transfected one or more constructs encoding the viral receptor and co-receptor (i.e., CD4 and CCR5, respectively), and the Ω-fragment of β-galactosidase. The cells are mixed and incubated in the presence or absence of inhibitors for varying times and at varying temperatures during which the viral envelope protein binds to the CD4/CCR5 complex. Cell fusion brings the α-fragment and Ω-fragment of β-galactosidase into proximity where the α-fragment mediates the tetramerization of 1-fragments into a functional β-galactosidase. The resultant functional β-galactosidase is then quantified following the addition of any β-galactosidase appropriate substrate known in the art.

While many of the anti-viral compounds currently used therapeutically target post-entry steps in the virus lifecycle, use of entry inhibitors have the advantage of completely preventing infection. Therefore, there is a need for an efficient and reliable method to rapidly identify inhibitors of viral entry or fusion events. Current methods for high throughput screening for such inhibitors have significant disadvantages. Ligand-receptor competition assays or cell-based assays for cell-cell fusion, virus entry, or single cycle reporter virus infection do not directly measure the fusion event, but rather measure a secondary result of the fusion. See, e.g., Vodicka et al., *Virology* 233: 193-98 (1997). For example, in one assay system, fusion is measured subsequent to the target virus integrating into the host genome and expressing the detector molecule. If the virus fails to integrate for a reason independent of the fusion event, the detector molecule would not be expressed, and thus result in a false positive reading for the compound being tested. Other methods using diffusable dyes to measure fusion are not amenable for high-throughput analysis. See, e.g., Raviv, Y., et al., *Virology* 293: 243-51 (2002). The alpha-complementation fusion assay provided herein is a means to directly detect viral envelope protein-mediated fusion while eliminating the difficulty of false positives and is suitable for high-throughput screening.

Viral Envelope Proteins and Receptors

A viral envelope protein binds one cell with a complementary receptor on the other to mediate fusion of the membranes of the two cells. The complementary receptor may be a single molecule or be more than one molecule. The binding of the viral envelope protein to its complementary receptor initiates the fusogenic process that subsequently results in fusion of the two cells into one hybrid cell.

Any viral envelope protein from a virus that mediates membrane fusion can be used with the present method. As used herein, the term "viral envelope protein" refers to a full-length protein, fragment, analog, or derivative thereof that binds to a complementary receptor or a complementary receptor and one or more co-receptors to mediate cell fusion. Typically, a viral envelope protein originates from an enveloped virus. An enveloped virus is one that is encapsulated by a lipid bilayer or surrounded by a lipid bilayer, where present on the surface of the encapsulating or surrounding lipid bilayer is at least one type of surface protein required for cell fusion. The surface protein may be a glycoprotein. The surface protein participates in receptor-mediated entry of the enveloped virus into the target cell via fusion of the viral envelope with the target cell membrane. Typically, a viral envelope protein monomer forms trimeric complexes that then bind the viral envelope protein receptor and mediate fusion. Viral envelope proteins useful in the present method can include, but are not limited to surface proteins from a number of different types of enveloped viruses, including, but not limited to herpesviruses, coronaviruses, paramyxoviruses, retroviruses, orthomyxoviruses, togaviruses, flaviviruses, filoviruses, retroviruses, poxviruses, hepadnaviruses, iridoviruses, rhabdoviruses, bunyaviruses, and arenaviruses. Viral envelope proteins of interest may also include those of subviral agents, including deltaviruses and prions. Specific embodiments of viruses include, but are not limited to HIV, HTLV, influenza, vesicular stomatitis virus (VSV), and Ebola virus. Specific embodiments of viral envelope proteins include, but are not limited to: HIV gp160 protein, Ebola GP protein, HTLV SU protein, influenza HA protein, and the like.

Any viral envelope protein receptor can be used with the present method. As used herein, the term "viral envelope protein receptor" refers to a full-length protein, fragment, analog, or derivative thereof that binds a complementary viral envelope protein to mediate cell fusion. A viral envelope protein receptor can be any form of receptor recognized in the art. Examples include, but are not limited to a single transmembrane protein, a multiple transmembrane protein, a glycoprotein, a G-coupled protein, or a glycosylphosphatidyinositol-anchored protein. A viral envelope protein receptor may alone be sufficient to mediate cell fusion via interaction with the viral envelope protein or may require one or more co-receptors to mediate cell fusion. A viral envelope protein receptor can be one recognized functionally in the art, but not yet identified molecularly. For example, a viral envelope protein receptor can be recognized as expressed on a particular cell type or a particular cell line as determined by fusogenic activity with cells or virions expressing the viral envelope protein while its exact identity remains unknown. Specific embodiments of viral envelope protein receptors include CD4 (for HIV), terminal sialic acid residues present on cell surface glycoproteins and glycolipids (for influenza HA), and the like.

Any viral envelope protein co-receptor can be used with the present methods. As used herein, the term "viral envelope protein co-receptor" refers to one or more full-length proteins, fragments, analogs, or derivatives thereof that are necessary, but not sufficient for the binding of a viral envelope protein of interest to mediate cell fusion. A viral envelope protein co-envelope receptor includes, but is not limited to a single transmembrane protein, a multiple transmembrane protein, a glycoprotein, a G-coupled protein, a glycosylphosphatidyinositol-anchored protein or a secreted protein. Specific embodiment include CXCR4 and CCR5.

Any fragment of the viral envelope protein, its receptor, or its co-receptor can be used in the methods herein. As used herein, the term "fragment" refers to any biologically active fragment of the proteins described herein. Such fragments can include only a portion of the full-length sequence of the protein and yet possess the same function, possibly to a greater or lesser extent. For example, fragments comprising deletion mutants of a viral envelope protein receptor, viral envelope protein co-receptor, or viral envelope protein can be designed and expressed by well known laboratory methods. Such fragments can be evaluated for fusogenic properties routinely using the assays provided herein as an indicator of biological activity.

Likewise, any analog or derivative of the viral envelope protein, its receptor, or its co-receptor can be used in the methods herein. As used herein, the term "analog or derivative" refers to substituted proteins characterized by the ability to bind a viral envelope protein, its receptor (or co-receptor) as indicated. Such mutations and substitutions can be designed and expressed by well-known laboratory methods. Such fragments can be evaluated for fusogenic properties routinely using the assays provided herein as an indicator of biological activity. Furthermore, any combination of biologically functional molecules may be used to mediate the cell fusion event. Biologically functional molecules can include full-length proteins, fragments, analogs, or derivatives thereof. Such biologically functional molecules can multimerize for activity or be active in monomer form.

Cells

Any cell can be used with the present method. As used herein, the term "cell" includes a biological cell (e.g., HeLa) and a non-biological cell (e.g., a lipid vesicle or virion). The cell can be human or nonhuman. The cell can be freshly isolated (i.e., primary) or derived from a short term- or long term-established cell line. Exemplary biological cell lines include NIH-3T3 murine fibroblasts, quail QT6 cells, canine Cf2Th thymocytes, Mv1 Lu mink lung cells, Sf9 insect cells, primary T-cells, human T-cell lines (e.g., H-9), U-87 MG glioma, SCL1 squamous cell carcinoma cells, CEM, HeLa epithelial carcinoma, Chinese hamster ovary (CHO) cell, SF33 cell and 293T cell. Such cell lines are described, for example, in the Cell Line Catalog of the American Type Culture Collection (ATCC, Rockville, Md.). Non-biological cells can include lipids, liposomes, and encapsulation procedures are known in the art.

A cell can express the viral envelope protein receptor, viral envelope protein co-receptor, or viral envelope necessary for cell fusion endogenously or exogenously (e.g., as a result of the stable transfer of genes). Endogenous expression by a cell as provided herein can result from constitutive or induced expression of endogenous genes.

Exogenous expression by a cell as provided herein can result from the introduction of the nucleic acid sequences encoding a viral envelope protein receptor, viral envelope protein co-receptor or viral envelope protein. Transformation may be achieved using viral vectors, calcium phosphate, DEAE-dextran, electroporation, cationic lipid reagents, or any other convenient technique known in the art. The manner of transformation useful in the present invention are conventional and are exemplified in CURRENT PROTOCOLS IN MOLECULAR BIOLOGY (Ausubel, F. M., et al., eds. 2000). Exogenous expression of the viral envelope protein, its receptor, and, when applicable, its co-receptor can be transient, stable, or some combination thereof. Exogenous expression can be enhanced or maximized by co-expression with one or more additional proteins, e.g., HIV rev. Exogenous expression can be achieved using constitutive promoters, e.g., SV40, CMV, and the like, and inducible promoters known in the art. Suitable promoters are those which will function in the cell of interest.

In one embodiment, a first cell stably expresses the viral envelope protein and displays it on the cell surface. Therefore, a first cell may comprise a coding sequence for the viral envelope protein stably integrated into its genome in a manner such that it is expressed in the first cell and directed to the cell surface where it is displayed in a functional manner. The first cell can include an expression construct made up of a suitable promoter operably linked to the viral envelope protein encoding sequence, where the expression construct is integrated into the first cell genome in a manner such that the envelope coding sequence is expressed in the cell and the expressed viral envelope protein is transported to the cell surface where it is displayed in a functional manner. In one embodiment, the viral envelope protein is HIV gp160 and is co-expressed with the HIV rev protein.

In another embodiment, a second cell stably expresses the viral envelope protein receptor (and co-receptor, if applicable) and displays it on the surface of the second cell. Therefore, a second cell may comprise a coding sequence for the viral envelope protein receptor (and co-receptor, if applicable) stably integrated into its genome in a manner such that it is expressed in the second cell and directed to the cell surface where it is displayed in a functional manner. The second cell can include an expression construct made up of a suitable promoter operably linked to the viral envelope protein receptor-encoding sequence, where the expression construct is integrated into the second cell genome in a manner such that the viral envelope protein receptor-encoding sequence is expressed and the expressed viral envelope protein receptor is transported to the cell surface where it is displayed in a functional manner.

The level of expression of the viral envelope protein, its receptor, and when applicable, its co-receptor is that required to mediate the cell fusion event. One of ordinary skill in the art can determine the required level of expression for fusogenic activity using assays routinely employed in the art.

Also provided herein are vectors or plasmids containing a nucleic acid that encodes for a viral envelope protein receptor, viral envelope protein co-receptor, or viral envelope protein. Suitable vectors for use in eukaryotic and prokaryotic cells are known in the art and are commercially available or readily prepared by a skilled artisan. Additional vectors can also be found, for example, in CURRENT PROTOCOLS IN MOLECULAR BIOLOGY (Ausubel, F. M., et al., eds. 2000) and Sambrook et al., "Molecular Cloning: A Laboratory Manual," 2nd ED. (1989), the teachings of which are incorporated herein by reference. In one embodiment, a viral envelope protein receptor or viral envelope protein is encoded in a different vector or plasmid than the reporter molecule fragment. In another embodiment, the viral envelope protein receptor or viral envelope protein is encoded in the same vector or plasmid as the reporter molecule fragment.

Once the nucleic acid is incorporated into a first or second cell as provided herein, the cell can be maintained under suitable conditions for expression of the exogenous viral envelope protein or viral envelope protein receptor, and the reporter molecule fragment. Generally, the cells are maintained in a suitable buffer and/or growth medium or nutrient source for growth of the cells and expression of the gene product(s). The growth media are not critical to the invention, are generally known in the art and can include sources of carbon, nitrogen and sulfur. Examples include Luria broth, Superbroth, Dulbecco's Modified Eagles Media (DMEM), RPMI-1640, M199 and Grace's insect media. The growth media may contain a buffer, the selection of which is not critical to the invention. The pH of the buffered media can be selected and is generally one tolerated by or optimal for growth for the host cell.

A first cell as provided herein comprises a viral envelope protein and a first reporter molecule fragment. Therefore, the first cell represents the virus particle or virally-infected cell for which the test agent is being assayed for inhibitory activity. In one embodiment, a first cell is a eukaryotic cell, where the eukaryotic cell is a cell that can be grown in culture, using standard laboratory procedures and media well known to those of skill in the art. The first cell may be any cell that is not susceptible to toxic effects of chronically expressing viral envelope proteins, that permit cell surface expression of such proteins, and that does not express endogenous proteins that inhibit cell fusion. The first cell is a cell that does not express complete receptors (or co-receptors, if applicable) for the expressed viral envelope protein and therefore will not undergo fusion with itself. In one embodiment, the first cell is the HeLa epithelial carcinoma or the human 293T cell line.

A second cell as provided herein comprises a second reporter molecule fragment and a viral envelope protein receptor capable of binding to the viral envelope protein of the first cell. The second cell represents the target cell, i.e., the cell that the virus of interest enters. In one embodiment, a second cell is a eukaryotic cell, where the eukaryotic cell is a cell that can be grown in culture, using standard laboratory procedures and mediums well known to those of skill in the art. The second cell may be any cell that can stably express the complete viral envelope protein receptor (and co-receptor, if applicable) and a second reporter molecule fragment without toxic effects and that does not express endogenous proteins that inhibit cell fusion. The viral envelope protein receptor is expressed on the surface of the second cell and is one that is a cell surface receptor protein that is employed by the virus of interest for receptor mediated fusion entry. In one embodiment where a viral envelope protein is gp160, a viral envelope receptor is CD4, and a viral envelope protein co-receptor is CCR5 or CXCR4. In one embodiment, a second cell is a 293T cell, SF33 cell, HeLa cell, or the like.

A first or second cell as provided herein can be prepared using standard molecular biology procedures known to those of skill in the art, where the particular protocol employed to make the first or second cell is not critical to the methods and compositions provided herein. A representative protocol for the preparation of a first and second cell is described in Example section. Thus, featured herein are methods of making a first cell, which comprises contacting a cell with a first expression construct containing a suitable promoter operably linked to a viral envelope protein coding sequence, whereby the viral envelope protein is expressed in a functional form on a cell surface; and contacting a cell with a second expression construct containing a suitable promoter operably linked to a first reporter molecule fragment coding sequence, whereby the reporter molecule fragment is expressed. Also featured is a method of making a second cell, which comprises contacting a cell with a first expression construct containing a suitable promoter operably linked to a viral envelope protein receptor coding sequence, whereby the viral envelope protein is expressed in a functional form on a cell surface; and contacting a cell with a second expression construct containing a suitable promoter operably linked to a second reporter molecule fragment coding sequence, whereby the reporter molecule fragment is expressed.

Reporter Molecules

Reporter molecules are any molecule capable of alpha complementation. In alpha complementation, a reporter molecule is a molecule whose activity is lost if the essential portions or subunits are separated, and whose activity is restored when the portions are expressed in proximity to one another. The activity can be enzymatic, catalytic, and the like, where such activity can be measured in at least a semi-quantitative fashion. Enzymes known to reform from peptide fragments and regain enzymatic activity include, but are not limited to ribonuclease (Richards, et al., *J. Biol. Chem.* 234: 1459 (1959)), staphylcoccal nuclease (Light, et al., *J. Biol. Chem.* 249: 2285 (1974)), and β-galactosidase (Langley and Zabin, *Biochemistry* 15: 4866 (1976)).

A first reporter molecule fragment can be one portion of any molecule capable of alpha complementation. In one embodiment, the reporter molecule is β-galactosidase (hereafter β-gal) and the first reporter molecule fragment is the α-fragment of β-gal. β-gal is a tetrameric protein having a molecular weight (MW) equal to 540,000 daltons. The four identical monomers consist of 1021 amino acids, each with a MW of 116,000 daltons. The monomeric protein is divided into three regions; (1) the N-terminal proximal segment (the α-region), (2) a middle region, and (3) a C-terminal distal segment (the Ω-region). The amino-terminal domain of the protein, otherwise known as the α-domain, is about 100 amino acids and mediates tetramerization. The carboxy-terminal domain, otherwise known as the Ω-domain, contains the active site of the enzyme. When individually expressed as separated domains, the α-domain and Ω-domain are enzymatically inactive. However, when the two fragments are present in a single cell, they re-associate to form an active enzyme, a phenomenon termed α-complementation.

A second reporter molecule fragment is the complementary domain to the first reporter molecule fragment, where the two fragments originate from a molecule capable of alpha complementation whose. In one embodiment, the reporter molecule is β-galactosidase (hereafter β-gal) and the second reporter molecule fragment is the Ω-fragment of β-gal.

Cell Fusion Inhibitors

Cell fusion inhibitor molecules are those molecules that reduce or eliminate the cell fusion event. Such inhibition can occur through direct binding of one or more critical binding residues of a viral envelope protein, its receptor, or when applicable, its co-receptor or through indirect interference including steric hindrance, enzymatic alteration of the fusogenic proteins (i.e., viral envelope protein and its complementary receptors and co-receptors (if applicable)), and the like. As used herein, the term "cell fusion inhibitor molecule" includes both protein and non-protein moieties. In one embodiment, the agent is a small molecule. In another embodiment, the agent is a protein.

A variety of different test inhibitory molecules may be identified using the method as provided herein. Test cell fusion inhibitory molecules can encompass numerous chemical classes. In certain embodiments, they are organic molecules, preferably small organic compounds having a molecular weight of more than 50 and less than about 2,500 daltons. Test cell fusion inhibitory molecules can comprise functional groups necessary for structural interaction with proteins, particularly hydrogen bonding, and may include at least an amine, carbonyl, hydroxyl or carboxyl group, preferably at least two of the functional chemical groups. The test cell fusion inhibitory molecules can comprise cyclical carbon or heterocyclic structures and/or aromatic or polyaromatic structures substituted with one or more of the above functional groups. Test cell fusion inhibitory molecules are also include biomolecules like peptides, saccharides, fatty acids, steroids, purines, pyrimidines, derivatives, structural analogs or combinations thereof. Test cell fusion inhibitory molecules of interest also can include peptide and protein agents, such as antibodies or binding fragments or mimetics thereof, e.g., Fv, F(ab')$_2$ and Fab.

Test cell fusion inhibitory molecules also can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Exemplary compounds useful in the present invention include, but are not limited to the compounds of U.S. Pat. Nos. 6,096,917; 6,100,426; 6,103,922; 6,103,923; 6,124,494; 6,127,422; 6,156,924; 6,175,034; 6,180,815; and 6,180,816. An exemplary compound is a compound of the formula:

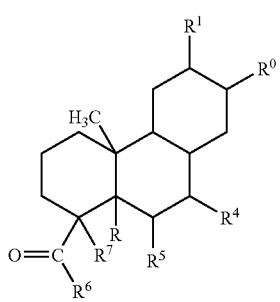

wherein:

R is hydrogen or R and $R^6$ combine to form a bond;

$R^0$ and $R^1$ are independently hydrogen, hydroxy, $C_1$-$C_6$ alkyl, $C_1$-$C_6$ alkoxy, hydroxy ($C_1$-$C_6$ alkyl), sulfhydryl, sulfamyl, —$SO_2$—$C_1$, —S—C(O)—N(CH$_3$)$_2$, amino, $C_1$-$C_4$ alkylamino, di($C_1$-$C_4$ alkyl)amino, $C_1$-$C_4$ alkylstilfonylamino, di($C_1$-$C_4$ alkylsulfonyl)amino —$X^0$—O—C(O)—$C_1$-$C_4$, alkyl, —O—($X^1$)—$X^2$, —C(O)—$X^3$, —N—C(O)—$R^2$ or —O—$R^3$;

$X^0$ is a bond or divalent($C_1$-$C_6$) alkyl);

$X^1$ is an amino acid;

$X^2$ is hydrogen or an amino protecting group;

i is 1, 2, or 3;

$X^3$ is $C_1$-$C_6$ alkyl, $C_1$-$C_6$ alkoxy, halo($C_1$-$C_6$ alkyl), hydroxy($C_1$-$C_6$ alkyl) or phenyl;

$R^2$ is $C_1$-$C_4$ alkyl, $C_1$-$C_4$ alkoxy, halo($C_1$-$C_4$ alkyl), hydroxy($C_1$-$C_4$ alkyl), phenyl, p-methoxy-phenyl, p-fluoro-phenyl, naphthlyl, pyridyl, thiazolyl, oxazolyl, thenyl, furyl, tetrahydrofuryl or cyclohexyl;

$R^3$ is $C_1$-$C_6$ alkenyl, —CH$_2$—$R^{3a}$, —C(O)—$R^{3b}$, —C(S)—$R^{3c}$, —C(CH$_3$)$_2$C(O)NH$_2$, phenyl or a group of the formula:

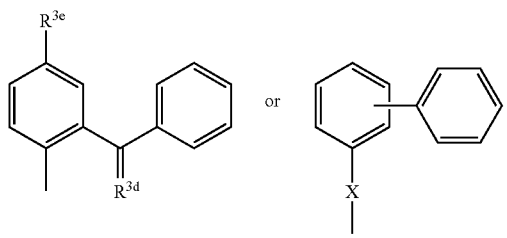

$R^{3a}$ is phenyl, p-fluorophenyl, pyridyl, pyrrolidinyl, piperidinyl, piperazinyl, morpholinyl, N—($C_1$-$C_4$ alkoxycarbonyl)piperidinyl, N-(trifluoromethyl)-piperidinyl, thiazolyl, oxazolyl, imidazolyl, isothiazolyl, isooxazolyl, quinolyl, isoquinolyl, thienyl, furyl, tetrahydrothienyl, tetrahydrofuryl, cyclohexyl, cyclopentyl, cyclopropyl or naphthyl;

$R^{3b}$ is pyrrolidinyl, piperidinyl, piperatinyl, morpholinyl, N—($C_1$-$C_4$ alkoxycarbonyl)piperidinyl, N-(trifluoromethyl) piperidinyl, benzyloxy, pyridylmethyloxy, $C_1$-$C_6$ alkoxy, halo($C_1$-$C_4$ alkoxy), amino, $C_1$-$C_4$ alkylamino or di($C_1$-$C_4$ alkyl)amino;

$R^{3c}$ is amino, $C_1$-$C_4$ alkylamino or di($C_1$-$C_4$ alkyl)amino;

$R^{3d}$ is oxygen, hydroximino, hydrazino or —CHZ;

Z is hydrogen, $C_1$-$C_4$ alkyl, holgen, di($C_1$-$C_4$ alkyl)amino, $C_1$-$C_4$ alkoxycarbonyl, carborunoyl ($C_1$-$C_4$, alkyl), N—($C_1$-$C_4$ alkyl)carbonmoyl or N,N-di($C_1$-$C_4$ alkyl)carbamoyl;

$R^{3e}$ is hydrogen, nitro or trifluoromethyl;

X is a bond or —(CH$_2$—;

$R^4$ is hydrogen, hydroxy, amino, $C_1$-$C_4$ alkylamino, di($C_1$-$C_4$ alkyl)amino, $C_1$-$C_4$ allcoxy, =O, —O—S(CH$_3$)$_2$C(CH$_3$)$_3$, $C_2$-$C_6$ alkanoyloxy, N—($C_2$-$C_6$ alkanoyl)amino, =N—$R^4$ or $R^4$ and $R^6$ combine to form a bond; $R^5$ is hydroxy amino, $C_1$-$C_4$ alkylamino, di($C_1$-$C_4$ alkyl)amino, $C_1$-$C_4$ alkoxyy pyridylmethoxy, benzyloxy, piperazinyl, N-(methyl)piperazinyl or —O—CH$_2$—C(O)—$R^{5a}$, $R^{5a}$ is hydroxy or $C_1$-$C_4$ alkoxy;

$R^6$ is hydrogen, halo, $C_1$-$C_4$ alkyl or =O;

$R^7$ is hydrogen or $C_1$-$C_4$ alkyl;

$R^8$ is hydroxy, halo, $C_1$-$C_6$ alkoxy, pyrrolidinyl, piperidinyl, piperazinyl, 4-methy-piperazinyl, morpholinyl or —N($R^9$)—$R^{10}$;

$R^9$ is hydrogen or methyl;

$R^{10}$ is-(divalent $C_1$-$C_6$ alkyl)-$R^{10a}$;

$R^{10a}$ is pyridyl, with the proviso that $R^6$ cannot combine with both $R^4$ and R to form a bond;

or a pharmaceutically acceptable salt thereof.

Another exemplary compound is a compound of the formula:

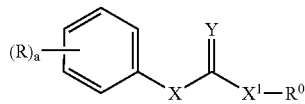

wherein:

a is 1, 2 or 3;

X is a bond, —NH—, CH$_2$—, —O— or —S—;

Y is oxygen, sulfur or nitrogen;
R is halo or $C_1$-$C_4$ alkyl or $C_1$-$C_4$ alkoxy;
$X^1$ is —O—, —N($R^1$)— or —$CH_2$—;
$R^0$ is a group of the formula:

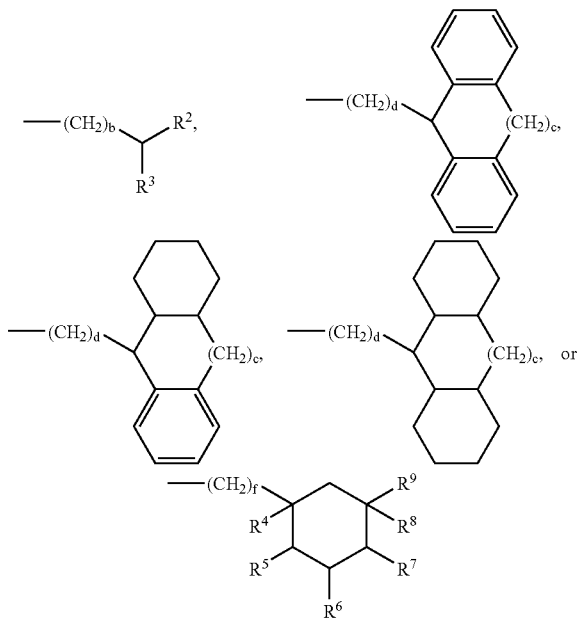

where:
$R^1$ is hydrogen, $C_1$-$C_4$ alkyl, benzyl or pyridyl($C_1$-$C_4$ alkyl), thienyl($C_1$-$C_4$ alkyl) or furyl($C_1$-$C_4$ alkyl);
each b, d and f are independently 1, 2 or 3;
c is 0, 1 or 2;
$R^2$ and $R^3$ are independently hydrogen, phenyl, pyridyl, thiazolyl, quinolyl, tetrahydroquinolyl, cyclohexyl, cyclohexenyl or phenyl or pyridyl substituted with halo, $C_1$-$C_4$ alkyl or $C_1$-$C_4$ alkoxy;
$R^4$ is hydrogen, $C_1$-$C_4$ alkyl or phenyl;
$R^5$ is hydrogen or $R^5$ and $R^6$ combine to form a bond;
$R^6$ and $R^7$ are independently hydroxy, —OC(O)$CH_3$, =O, —OC(O)NH$R^{6a}$, —O—($R^{6b}$)x or $R^6$ and $R^7$ combine to form a bond;
$R^{6a}$ is hydrogen, $C_1$-$C_4$ alkyl, phenyl or benzyl;
$R^{6b}$ is an amino acid;
x is 1, 2 or 3;
$R^8$ and $R^9$ are independently hydrogen or $C_1$-$C_4$ alkyl; with the proviso that when $R^5$ and $R^6$ combine to form a bond, $R^7$ must be hydrogen, and when $R^6$ and $R^7$ combine to form a bond, $R^5$ must be hydrogen;
or a pharmaceutically acceptable salt thereof.

Specific embodiments of cell fusion inhibitor molecules include AMD3100 (*Nat. Med.* 4: 72-77), Tak779 (*Proc. Nat'l Acad. Sci. U.S.A.* 96: 5698-5702), Schering C (*Proc. Nat'l Acad. Sci. U.S.A.* 98: 12718-12723), C34 peptide (*Cell* 89: 263-273), T20 peptide (*Proc. Nat'l Acad. Sci. U.S.A.* 91: 9770-9774), and CD4-Ig (*AIDS Res. Hum. Retrovir.* 11: 533-539).

Also featured herein is structural information descriptive of a cell fusion inhibitor molecule identified by the processes described herein. In certain embodiments, information descriptive of cell fusion inhibitor molecule structure (e.g., chemical formula or sequence information) sometimes is stored and/or renditioned as an image or as three-dimensional coordinates. The information sometimes is stored and/or renditioned in computer readable form and sometimes is stored and organized in a database. In certain embodiments, the information may be transferred from one location to another using a physical medium (e.g., paper) or a computer readable medium (e.g., optical and/or magnetic storage or transmission medium, floppy disk, hard disk, random access memory, computer processing unit, facsimile signal, satellite signal, transmission over an internet or transmission over the world-wide web).

Detection of Cell Fusion

Any fusogenic event can be detected by the methods and compositions provided herein. Cell fusion detected by the methods and compositions provided herein can occur between two cells that express the complementary viral envelope protein and receptor (and co-receptors, if applicable) exogenously, endogenously, or some combination thereof. The methods provided herein are also useful in detecting fusion that occurs within a cell, such as that occurring by SNARES.

In one embodiment, the methods provided herein permit a quantitation of fusogenic activity between cells that express the complementary viral envelope protein and receptor (and co-receptors, if applicable) exogenously, endogenously, or some combination thereof. In another embodiment, the methods provided herein are useful in identifying a cell as expressing an endogenous complementary viral envelope protein receptor by screening for fusogenic activity with a cell that exogenously expresses a particular viral envelope protein. In yet another embodiment, the methods provided herein permit the identification of biologically active fragments, analogs, and derivatives of exogenously expressed viral envelope proteins, viral envelope protein receptors (or co-receptors, if applicable). Additionally, a library of potential receptor molecules can be expressed in, for example, a second cell while a first cell expresses a fusogenic viral envelope protein, permitting a screening for new receptors for the fusogenic viral envelope protein.

First and second cells as provided herein are contacted using any convenient protocol. In one embodiment, the first and second cells are placed into a container that can hold a volume of a fluid medium, e.g., a well of a 96-well plate or 384 well plate, or an analogous structure. The first and second cells can be contacted in any volume with any cell number that will permit accurate detection of cell fusion events. In one embodiment, the total number of cells present ranges from about 1,000 to about 100,000 cells. In one embodiment, the reaction volume ranges from about 20 to 200 microliters. The cells can be contacted for any period of time. In one embodiment, the time of contact ranges from one hour to eight hours, with a preferred time of four hours. The first and second cells can be contacted in medium at any pH that is permissive for cell fusion. The first and second cells can be contacted at various temperatures. In one embodiment, the temperature for contact of the first and second cells often ranges from 25° C. to 38° C., with a temperature of 37° C. typically utilized. When desirable, the first and second cells may be agitated to ensure adequate mixing and presentation of viral envelope protein to its receptor.

In another embodiment, multiple sets of first and second cells are employed in the cell fusion assay with each set using a reporter molecule generating a distinct signal to create a multiple complementation assay. A multiple complementation assay can permit a quantitative examination of qualitative differences in binding affinities, binding specificity, competitive inhibition or enhancement, and the like between the complementary viral envelope protein and its receptor (and co-receptor, if applicable).

The presence or absence of cell fusion is determined by the detection of the presence or absence of a signal produced by the functional reporter molecule, whereby the presence of cell fusion is detected by the presence of a signal and the absence of cell fusion is detected by the absence of signal. The functional reporter molecule is formed when the first reporter molecule fragment and the second reporter molecule fragment combine. The particular detection protocol employed necessarily varies depending on the nature of the directly detectable product. For example, where the detectable product is a fluorescent protein, the lysate is irradiated with light of an appropriate wavelength to excite the fluorescent protein and emission from the fluorescent protein is detected.

In one embodiment, the functional reporter molecule is an enzyme whose activity can be monitored by the appearance of a product of the enzymatically catalyzed reaction or by disappearance of the enzyme substrate. In another embodiment, the functional reporter molecule can be detected without addition of exogenous substrate by measurement of some endogenous property (e.g., luminescence, chemiluminescence).

In embodiments where the functional reporter molecule is an enzyme that converts a substrate to a detectable product, the detection step typically first requires contacting the cell lysate with a substrate for the reporter enzyme. The substrate may be contacted with the lysate using any convenient protocol, e.g., by placing the lysate into a container having the substrate, by introducing the substrate into the lysate, etc. The nature of the particular substrate necessarily depends on the nature of the reporter enzyme which is present in the two fragments. For example, the substrate can be one that is converted by the reporter enzyme into a chromogenic product. Of interest in certain embodiments are substrates that are converted by the enzyme into a fluorescent product. The amount of substrate that is contacted with the lysate may vary, but typically ranges from about 1 femtomolar to 10 millimolar.

In one preferred embodiment, the functional reporter molecule is β-gal. Representative substrates that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbel-liferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galacto-pyranoside, 5-bromo-4-chloro-3-indolyl-β-D-galactopynanoside, resorufin-β-D-galactopyranoside, 7-hydroxy-4-trifluoromethyl coumarin, Ω-nitrostyryl-β-D-galactopyranoside, and flourescein-β-D-galactopyranoside. Manning et al., U.S. Pat. No. 5,444,161.

The substrate conversion can be evaluated in whole cells or in lysate depending on the nature of the substrate and the final detectable product as is known in the art.

In one embodiment, the lysate is evaluated for the presence or absence of detectable product following a predetermined incubation period, where this incubation period typically ranges from about 1 minute to about 2 hours. The particular detection protocol employed varies depending on the nature of the detectable product. For example, where the detectable product is a fluorescent product, the detection protocol employs the use of a fluorescent light detection means, e.g., a fluorescent light scanner, which can scan the lysate for the presence of fluorescent signal. The presence or absence of detectable signal from the signal producing system, e.g., detectable product in the lysate, is then used to derive information as to whether cell fusion occurred. The presence of a signal in the lysate is indicative of cell fusion. The signal can be correlated to the cell fusion event in a qualitative or quantitative manner. One also can employ a threshold value, whereby any signal above the threshold value represents insufficient activity and any signal below the threshold value represents sufficient activity. One also can evaluate the signal in a quantitative or a semi-quantitative manner, in which the amount of signal detected is used as a direct indication of the level of cell fusion events. The amount of signal detected may be linear or non-linear relative to the amount of cell fusion depending on the sensitivity of the reporter molecule and substrate employed. In one embodiment, a larger amount of signal indicates a greater amount of cell fusion, such that the amount of signal has a direct relationship with the amount of cell fusion.

The above signal evaluation may be accomplished using any convenient means. Thus, the signal may be subjectively evaluated by comparing the signal to a set of control signals. The evaluation may be done manually or using a computing or data processing means that compares the detected signal with a set of control values to automatically provide a value for the cell fusion activity. Quantified interactions can be expressed in terms of a concentration of signal molecule, test inhibitor molecule (as described in the section below), or protein component required for emission of a signal that is 50% of the maximum signal ($IC_{50}$). Also, quantified interactions can be expressed as a dissociation constant ($K_d$ or $K_i$) using kinetic methods known in the art.

Detection of Cell Fusion Inhibitor Molecules

Inhibitors of the cell fusion detected by the methods and compositions provided herein can be identified by quantitating the fusogenic activity between two cells that express the complementary viral envelope protein and receptor (and co-receptors, if applicable) exogenously, endogenously, or some combination thereof in the presence or absence of the test inhibitor molecule.

Also provided herein is a method for identifying a cell fusion inhibitor molecule, which comprises contacting a system comprising a first cell and a second cell with a test molecule. The first cell comprises a first reporter molecule fragment and a viral envelope protein while the second cell comprises a second reporter molecule fragment and a viral envelope protein receptor capable of binding to the viral envelope protein of the first cell. The first reporter molecule fragment and the second reporter molecule fragment of the first and second cells, respectively, combine to form a functional reporter molecule upon fusion of the first cell with the second cell. The presence or absence of functional reporter molecule is detected by the presence or absence of a signal produced by the functional reporter molecule. The test molecule is identified as a cell fusion inhibitor molecule when the signal produced by the functional reporter molecule in the system contacted with the test molecule is different than the signal produced in a system not contacted by the test molecule. As used herein, the term "different" refers to a reduction or elimination of signal produced by the functional reporter molecule in the presence of the test inhibitor molecule as compared to the signal produced by the functional reporter molecule in the absence of the test inhibitor molecule.

In the method for identifying a cell fusion inhibitor molecule, the first and second cells are contacted with each other in the presence of a test cell fusion inhibitory molecule as described above. A test cell fusion inhibitory molecule may be present in one of the first or second cell compositions prior to the contacting of the two cells, added simultaneously or after the contacting of the first and second cells. In one embodiment, the manner in which the first and second cell populations are combined with the test cell fusion inhibitory molecule is not critical, so long as the test cell fusion inhibitory molecules is present to prevent fusion of the first and second cells if it has inhibitory activity. In another embodiment, the test inhibitory molecule is added to a first or second cell population prior to contact with the second or first cell population, respectively.

A test cell fusion inhibitor molecule is identified as an inhibitor when it is capable of specifically inhibiting the fusion of an envelope protein with its corresponding receptor or receptor/co-receptor(s) by reducing the rate or amount of fusion mediated by a receptor or receptor/co-receptor cell contacting a viral envelope protein+ cell by at least 50%, often 60, 70, 80 or 90%, and sometimes 100%. In one embodiment, a cell fusion inhibitor molecule will inhibit only receptor-mediated fusion events without inhibiting non-receptor mediated fusion events. As used herein, the term "rate of cell membrane fusion" refers to the total quantity of cell membrane fused per unit time. The term "inhibit" refers to the capacity to at least impede the fusion of the viral envelope protein receptor+ cell with the viral envelope protein+ cell, where the molecules identified by the method provided herein may substantially, if not completely, prevent fusion of the viral envelope protein receptor+ cell with the viral envelope protein+ cell. It is contemplated that such inhibitors would also impede or substantially, if not completely, prevent the corresponding receptor mediated entry of the virus into the target cell.

The amount of test cell fusion inhibitory molecule that is present in the contact mixture may vary, particularly depending on the nature of the test cell fusion inhibitory molecule. In one embodiment, where the agent is a small organic molecule, the amount of cell fusion inhibitory molecule present in the reaction mixture can range from about 1 femtomolar to 10 millimolar. In another embodiment, where the agent is an antibody or binding fragment thereof, the amount of the cell fusion inhibitory molecule can range from about 1 femtomolar to 10 millimolar. The amount of any particular agent to include in a given contact volume can be readily determined empirically using methods known to those of skill in the art.

As described above, the presence or absence of detectable signal is determined from the fusion of the first and second cells. The signal can be correlated to the inhibitory activity of the test cell fusion inhibitory molecule and therefore is used to determine the inhibitory activity of a test cell fusion inhibitory molecule. In the method, the presence of signal indicates a lack of inhibitory activity by the test cell fusion inhibitory molecule since signal is only present when cell fusion occurs. As such, the absence of signal indicates that the test cell fusion inhibitory molecule possesses inhibitory activity or less signal when the test inhibitor molecule is added. Fusion inhibition can be expressed as % fusion, rate of fusion, $IC_{50}$, or $K_d$.

The above signal evaluation as a determination of the inhibitory activity may be accomplished using any convenient means. Thus, the signal may be subjectively evaluated by comparing the signal to a set of control signals. The evaluation may be done manually or using a computing or data processing means that The above cell fusion protocols are amenable to high throughput formats, by which is meant that the above cell fusion assays can be performed in an automated fashion to screen a plurality of different test cell fusion inhibitor molecules simultaneously. As such, large numbers of compounds can be screened using automated means at substantially the same time. In one embodiment, at least about 10,000 to 1,000,000 compounds can be screened simultaneously. In these high throughput formats, one or more of the above steps, including all of the steps, may be automated, including cell/test cell fusion inhibitor molecule contact, lysate production, signal detection and signal evaluation.

Cell Hybrids

Also provided is a cell hybrid that is a fusion product of a first cell and second cell. The cell hybrid has one or more nuclei and may have one contiguous membrane. The cell hybrid comprises a functional reporter molecule formed from the combination of a first reporter molecule fragment and a second reporter molecule fragment. The cell hybrid can also express a viral envelope protein and a viral envelope protein receptor capable of binding to the viral envelope protein simultaneously.

EXAMPLE 1

Cell Lines for use in Fusion Assay

All tissue culture medium was DMEM (BioWhittaker) supplemented with 10% FBS, 1% penicillin/streptomycin, and 1% HEPES. The envelope/alpha-expressing cells were made by transient transfection by the calcium phosphate method (as described below) or using lipofectamine 2000 (Invitrogen).

293T (ATCC cat #CRL-1573) or HeLa (ATCC cat #CCL-2) cells ($2.5 \times 10^6$) were seeded in 10 cm plates 24 hours prior to transfection. The next morning, cells were transfected with 21 µg of DNA, 7 µg pSCTZ-alpha-N85, 7 µg pRSV-Rev (Hope et al., *Proc. Nat'l. Acad. Sci. U.S.A.* 87: 7787-91 (1990)) and 7 µg of envelope expression vector (pSV-ADA, pSV-JRFL (Deng et al., *Nature* 381: 661-666 (1996)), or pCAGGS-SF33 (York-Higgins et al., *J. Virol.* 64: 4016-4020 (1990)).

pSCTZ-alpha-N85 is an expression vector for the alpha fragment of beta-galactosidase, consisting of the first 85 amino acids of beta-galactosidase under the control of the CMV promoter.

293T-omega cells were generated by stable transfection ($Ca_2PO_4$ method) (Graham, et al., *Virol.* 52: 456-67 (1973)) with pSCTZ-omega. pSCTZ-omega is an expression vector for the omega fragment of beta-galactosidase, consisting of the lac Z gene deleted from amino acid 10 to amino acid 37, also under the control of the CMV promoter (Moosmann and Rusconi, *Nucleic Acids Res.* 24: 1171-1172 (1996)). Clonal lines were tested for function in the fusion assay. The most active clone was selected and infected with a pMX-CD4 retroviral vector (Onishi, *Exp. Hematol.* 24: 324-329; Maddon et al., *Cell* 42: 93-104) that expresses CD4. A stable cell line was derived that expressed CD4, CXCR4, and omega and was then tested for function in the fusion assay. The most active clone was selected and infected with pBABE-CCR5 retroviral vector (Morgenstern and Land, *Nucleic Acids Res.* 18: 3587-96), a murine leukemia virus-based vector containing the CCR5 cDNA (described in Deng et al.). Clonal lines were produced and tested for function in the fusion assay. Several lines were selected that expressed differing levels of CCR5. A corresponding panel of HeLa cell lines was generated in a similar fashion. The assay can also be performed on a target cell line transiently transfected with pSCTZ-omega and pcDNA-CD4 (Lenburg and Landau, *J. Virol.* 67: 7238-45).

Experiments that required exact levels of CCR5 expression were done by transient transfection of a five-fold serial dilution of pcDNA-CCR5. 293T.CD4.omega cells were transiently transfected as above with varying ratios of pcDNA I/amp (Invitrogen) and pcDNA-CCR5 (Deng et al., *Nature* 381: 661-666) in a total of 20 µg DNA.

EXAMPLE 2

Protocol for Basic Fusion Reaction

Transfect 293 cells with expression vector for HIV envelope protein, B-gal-α and HIV-1 Rev. Vectors used express CCR5-specific Envs (JFRL, ADA) or CXCR4-specific Envs (SF33 or JC2) driven by the cytomegalovirus promoter. Transfect the cells by lipofection or calcium phosphate standard methods.

Two days later, remove the transfected cells from plates by incubating with phosphate-buffered saline containing 5 mM EDTA. The cells are then counted on hemocytometer.

Harvest 293-CD4.CCR5.omega cells with PBS/EDTA and count.

Mix the transfected 293-α cells with an equal number of 293-CD4.CCR5.omega cells. Distribute the mixture into the wells of a 96 well microtiter dish with a total of $2 \times 10^5$ cells per well. Spin dish briefly to lightly pellet cells together at the bottom of the tubes. Incubate at 37° C. for four hours in 5% $CO_2$ incubator.

Remove the plates from the water bath, spin 4000 rpm (Eppendorf tabletop centrifuge) for 1 minute to firmly pellet cells, aspirate medium, and add 100 µl of Galacto-Star lysis buffer (Perkin-Elmer). Mix well and incubate at room temperature for 5 minutes. Spin lysates 5 minutes at 4000 rpm and transfer 10 µl to a black 96-well plate (Costar). Add 100 µl of Galacto-Star substrate using a multi-channel pipettor. After 60 minutes, read β-gal activity in plates in a Packard TopCount luminometer for 15 s/well.

EXAMPLE 3

Protocol for Testing Fusion Inhibitors

Transfect 293 cells with expression vector for HIV envelope protein, B-gal-α and HIV-1 Rev. Vectors used express CCR5-specific Envs (JFRL, ADA) or CXCR4-specific Envs (SF33 or JC2) driven by the cytomegalovirus promoter. Transfect the cells by lipofection or calcium phosphate standard methods.

Two days later, remove the transfected cells from plates by incubating with phosphate-buffered saline containing 5 mM EDTA. The cells are then counted on hemocytometer.

Harvest 293-CD4.CCR5.omega cells with PBS/EDTA and count.

Prepare a microtiter plate by adding $2.5 \times 10^5$ 293-CD4.CCR5.omega cells to each well with a multi-channel pipettor or robot in a volume of 50 µl of medium. Add inhibitors at different concentrations to each of the wells, in duplicate. Include two wells without inhibitor as well as wells with known inhibitors as a positive control (e.g., AMD3100 for CXCR4 or TAK799 for CCR5 envelope glycoproteins). Incubate 30 minutes at 37° C./5% $CO_2$.

Add transfected 293-α cells expressing HIV-1 envelope protein.

After four hours, read β-gal activity as in Example 1.

EXAMPLE 4

Protocol for Small Molecule Fusion Inhibitor Screening

Transfect 293 cells with expression vector for HIV envelope protein, B-gal-α and HIV-1 Rev. Vectors used express CCR5-specific Envs (JFRL, ADA) or CXCR4-specific Envs (SF33 or JC2) driven by the cytomegalovirus promoter. Transfect the cells by lipofection or calcium phosphate standard methods.

Two days later, remove the transfected cells from plates by incubating with phosphate-buffered saline containing 5 mM EDTA. The cells are then counted on hemocytometer.

Add 10 µl small molecule inhibitors, diluted in DMSO, robotically to each well of the plates containing 293-CD4.CCR5.omega cells. Incubate 30 minutes.

Add transfected 293-α cells expressing HIV-1 envelope protein.

After four hours, read β-gal activity as in Example 1.

EXAMPLE 5

Transfection with Lipofectamine 2000

For a 10-cm dish transfection, first plate $2.5 \times 10^6$ 293T or HeLa cells per dish at 37° C. overnight.

In the morning of the 2nd day, set up the transfection per dish as (a) dilute 20 µg DNA in 1 ml Opti-MEM (or serum-free medium; (b) dilute 25 µl lipofectamine 2000 in 1 ml Opti-MEM (or serum-free medium) (can be made in bulk and aliquot later), RT for 5 min; (c) mix a and b and incubate at RT for 20 min; and (d) then aspirate the medium from the well, overlay 8 ml Opti-MEM (or serum-free medium). Overlay the DNA/lipid mixture on the cells. Put back in the 37° C. incubator for 4 hours.

Aspirate the medium. Add 10 ml per well fresh complete DMEM. Put into 37° C. incubator for 1-2 days.

EXAMPLE 6

Transfection with Calcium Phosphate Precipitated DNA

Solutions for transfection include: 2×HBS, pH 7.05-7.15 (1.0 g HEPES, 1.6 g NaCl, 0.074 g KCl, 0.025 g $Na_2HPO_4$ (for 7.$H_2O$ use 0.047 g); 2 M $CaCl_2$ (29.40 g $CaCl_2$ in 100 mls of dd$H_2O$); and chloroquine (10 mM) (store at −20° in the dark).

Split cells day before transfection into 10 cm plates such that they are 25% confluent on the next day; for COS use $1.5$-$2.0 \times 10^6$ cells; for 293 use $2.0 \times 10^6$.

On the next day, ethanol precipitate the DNA to be transfected: 80 µls TE, 10 µls 3M NaAc, 20 µgs plasmid (or 10 µgs of each of two different plasmids) and 250 µls Ethanol. Place on ice 5 mins and microfuge 5 mins. Suck off supernatant and add 0.8 Mlles ethanol, invert tube twice to wash without disturbing pellet. Take tubes into tissue culture hood and suck off supernatant carefully watching to see that the pellet does not get lost. Add 450 µLs sterile water, vortex and add 62 µLs $cal_2$.

Place 500 µLs 2X-HBO in a sterile plastic tube (model 2054, Becton-Dickinson). Add the cal$_2$/DNA solution dropwise from a Pasteur pipette at a rate of about 2 drops/second without mixing. Immediately after addition, flick several times to mix. Incubate 20 ins on ice.

Add the precipitate dropwise to a dish of cells (for 60 cm dishes use only 0.5 Mlles precipitate). A very fine precipitate should form that is visible only at high power magnification. The precipitate will not be easily visible until several hours after transfection.

Immediately, add 50 µLs chloroquine. For 293 cells, do not add chloroquine.

Incubate overnight. Change medium. Change medium next day also.

Harvest the cells 48-72 hr. after transfection. For virus assay, take supernatant after 72 h, filter, add polybrene to 8 µgs/ml and freeze or use right away.

Modifications may be made to the foregoing without departing from the basic aspects of the invention. Although the invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

What is claimed is:

1. A method for detecting the presence or absence of cell fusion, which comprises:
   contacting a system comprising a first cell with a second cell, wherein:
   the first cell comprises a first reporter molecule fragment and a viral envelope protein;
   the second cell comprises a second reporter molecule fragment and a viral envelope protein receptor capable of binding to the viral envelope protein of the first cell;
   the first cell is a HeLa cell and the second cell is a 293T cell, or the first cell is a 293T cell and the second cell is a HeLa cell;
   the first reporter molecule fragment and the second reporter molecule fragment combine to form a functional reporter molecule upon fusion of the first cell with the second cell; and
   detecting the presence or absence of a signal produced by the functional reporter molecule, whereby the presence of cell fusion is detected by the presence of a signal and the absence of cell fusion is detected by the absence of a signal.

2. The method of claim 1, wherein the first reporter molecule fragment and the second reporter molecule fragment are independently selected from an 1-fragment of β-galactosidase and an Ω-fragment of β-galactosidase.

3. The method of claim 1, wherein the second cell further comprises a viral envelope co-receptor protein.

4. The method of claim 3, wherein the viral envelope protein is HIV gp160, the viral envelope protein receptor is CD4, and the viral envelope protein co-receptor is CCR5.

5. The method of claim 4, wherein the first cell further comprises HIV rev.

6. The method of claim 3, wherein the viral envelope protein is HIV gp160, the viral envelope protein receptor is CD4, and the viral envelope protein co-receptor is CXCR4.

7. The method of claim 6, wherein the first cell further comprises HIV rev.

8. The method of claim 1, wherein the viral envelope protein is selected from the group consisting of HIV gp160, Ebola GP, HTLV SU, and influenza HA.

9. The method of claim 1, wherein the signal is chemiluminescent.

10. The method of claim 1, wherein the viral envelope protein is exogenously expressed.

11. The method of claim 1, wherein the viral envelope protein receptor is exogenously expressed.

12. The method of claim 1, wherein the viral envelope protein is endogenously expressed.

13. The method of claim 1, wherein the viral envelope protein receptor is endogenously expressed.

14. The method of claim 1, wherein the system comprises a molecule that inhibits cell fusion.

15. The method of claim 1, wherein one of the first and second reporter molecule fragment comprises a fragment of beta-galactosidase consisting essentially of an N-terminal alpha region of beta-galactosidase.

16. The method of claim 15, wherein the N-terminal alpha region of beta-galactosidase spans about amino acid 1 to about amino acid 100.

17. The method of claim 15, wherein the N-terminal alpha region of beta-galactosidase spans about amino acid 1 to about amino acid 85.

18. The method of claim 1, wherein one of the first and second reporter molecule fragment lacks a functional N-terminal alpha region of beta galactosidase.

19. The method of claim 18, wherein one of the first and second reporter molecule fragment lacks a region spanning about amino acid 10 to about amino acid 37.

* * * * *

UNITED STATES PATENT AND TRADEMARK OFFICE
CERTIFICATE OF CORRECTION

| | | |
|---|---|---|
| PATENT NO. | : 7,312,031 B1 | Page 1 of 1 |
| APPLICATION NO. | : 10/729069 | |
| DATED | : December 25, 2007 | |
| INVENTOR(S) | : Carsten Muenk, Anne Holland and Nathaniel Landau | |

It is certified that error appears in the above-identified patent and that said Letters Patent is hereby corrected as shown below:

In Col. 22 line 4 Claim 2, after "independently selected from an" and before "of β-galactosidase and an Ω-fragment" please replace [1-fragment] with -- α-fragment --.

Signed and Sealed this

Thirtieth Day of December, 2008

JON W. DUDAS
*Director of the United States Patent and Trademark Office*